United States Patent
Rittman, III et al.

(10) Patent No.: US 6,575,969 B1
(45) Date of Patent: Jun. 10, 2003

(54) COOL-TIP RADIOFREQUENCY THERMOSURGERY ELECTRODE SYSTEM FOR TUMOR ABLATION

(75) Inventors: William J. Rittman, III, Lynnfield, MA (US); Eric R. Cosman, Belmont, MA (US)

(73) Assignee: Sherwood Services AG, Schaffhausen (CH)

( * ) Notice: Subject to any disclaimer, the term of this patent is extended or adjusted under 35 U.S.C. 154(b) by 7 days.

(21) Appl. No.: 09/642,309

(22) Filed: Aug. 21, 2000

Related U.S. Application Data

(63) Continuation of application No. 08/562,986, filed on Nov. 24, 1995, now abandoned, which is a continuation-in-part of application No. 08/433,799, filed on May 4, 1995, now abandoned.

(51) Int. Cl.[7] ................................................. A61B 18/18

(52) U.S. Cl. ........................... 606/41; 128/898; 600/439

(58) Field of Search ................................. 606/27–31, 41, 606/42, 45, 48–50; 607/101, 102; 600/439, 461, 463; 128/898

(56) References Cited

U.S. PATENT DOCUMENTS

| | | | |
|---|---|---|---|
| 4,411,266 A | 10/1983 | Cosman | |
| 4,565,200 A | 1/1986 | Cosman | |

(List continued on next page.)

FOREIGN PATENT DOCUMENTS

| | | |
|---|---|---|
| DE | 2407559 | 2/1974 |
| EP | 0246350 A1 | 11/1987 |
| EP | 0310431 A2 | 4/1989 |

(List continued on next page.)

OTHER PUBLICATIONS

Cosman et al.: (1) "Theoretical Aspects of Radiofrequency Lesions in the Dorsal Root Entry Zone". *Neurosurgery* 15:945–950, 1984; (2) Cosman ER, Cosman BJ: "Methods of Making Nervous System Lesions", in William RH, Rengachary SS (eds): *Neurosurgery.* New York: McGraw–Hill, vol. III, pp. 2490–2498, 1984.

*Nuclear Magnetic Resonance Imaging—Basic Principles*, Stuart W. Young, Raven Press, New York, 1984.

(List continued on next page.)

*Primary Examiner*—Michael Peffley

(57) ABSTRACT

This patent application is a continuation-in-part of the patent application of the present authors related to target volume ablation in the body using a cooled-tip tissue-heating probe such as a fluid cooled (perfusion cooled) high frequency electrode. The present application relates in part to examples of specific embodiments of high frequency and radiofrequency electrode designs and heating and cooling system designs. It further describes embodiments in conjunction with 3-D or 2-D image data and computer graphic workstions to control, monitor, and pre-plan the process of target ablation. Specific examples of cooled-tip electrode constructions will be given which have utility for percutaneous or intraoperative cancerous tumor ablation. Cooled tip electrode systems with modular or separable components involving an insertion cannula, a radiofrequency electrode element, a cooling element, and a thermo-monitoring and/or radiofrequency connection electrode will be given. A high frequency and cooling system which is controlled and regulated based on the "thermally clamped tip" concept together with control of power, current, or other high frequency power parameters to pre-plan and control lesion size will be shown. Pre- or contemporaneous monitoring methods using CT, MR, ultrasound, and acoustic imaging or monitoring modalities in conjugation with the cooled tip high frequency ablation system will be exemplified. Variations in electrode design for specific target sites in the body will be described and illustrated.

14 Claims, 10 Drawing Sheets

U.S. PATENT DOCUMENTS

| | | |
|---|---|---|
| 4,576,177 A | 3/1986 | Webster, Jr. |
| 4,608,977 A | 9/1986 | Brown |
| 4,662,383 A | 5/1987 | Sogawa et al. |
| 4,832,024 A | 5/1989 | Boussignac et al. |
| 4,880,719 A | 11/1989 | Murofushi et al. |
| 4,961,435 A | 10/1990 | Kitagawa et al. |
| 4,966,597 A | 10/1990 | Cosman |
| 4,993,430 A | 2/1991 | Shimoyama et al. |
| 5,029,588 A | 7/1991 | Yock et al. |
| 5,103,804 A | 4/1992 | Abele et al. |
| 5,230,623 A | 7/1993 | Guthrie et al. |
| 5,267,994 A | 12/1993 | Gentelia et al. |
| 5,281,213 A | 1/1994 | Milder et al. |
| 5,323,778 A | 6/1994 | Kandarpa et al. |
| 5,330,518 A | 7/1994 | Neilson et al. |
| 5,334,193 A | 8/1994 | Nardella |
| 5,342,357 A | 8/1994 | Nardella |
| 5,348,554 A * | 9/1994 | Imran et al. .................. 606/41 |
| 5,370,675 A | 12/1994 | Edwards et al. |
| 5,383,876 A | 1/1995 | Nardella |
| 5,383,917 A | 1/1995 | Desai et al. |
| 5,385,148 A * | 1/1995 | Lesh et al. ............. 128/662.06 |
| 5,403,311 A | 4/1995 | Abele et al. |
| 5,409,000 A | 4/1995 | Imran |
| 5,409,006 A | 4/1995 | Buchholtz et al. |
| 5,433,739 A | 7/1995 | Sluijter et al. |
| 5,458,597 A | 10/1995 | Edwards et al. |
| 5,462,521 A | 10/1995 | Brucker et al. |
| 5,472,441 A | 12/1995 | Edwards et al. |
| 5,490,850 A | 2/1996 | Ellman et al. |
| 5,500,012 A | 3/1996 | Brucker et al. |
| 5,520,684 A | 5/1996 | Imran |
| 5,536,267 A | 7/1996 | Edwards et al. |
| 5,588,432 A * | 12/1996 | Crowley ............... 128/660.03 |
| 5,599,345 A * | 2/1997 | Edwards et al. .............. 606/41 |
| 5,647,871 A | 7/1997 | Levine et al. |
| 5,688,267 A | 11/1997 | Panescu et al. |
| 5,868,740 A | 2/1999 | LeVeen et al. |
| 5,921,982 A * | 7/1999 | Lesh et al. .................... 606/41 |
| 5,951,546 A | 9/1999 | Lorentzen |
| 6,053,912 A | 4/2000 | Panescu et al. |
| 6,241,725 B1 * | 6/2001 | Cosman ...................... 606/41 |
| 6,337,998 B1 | 1/2002 | Behl et al. |

FOREIGN PATENT DOCUMENTS

| | | |
|---|---|---|
| EP | 0608609 A2 | 8/1994 |
| WO | WO 93/24066 | 12/1993 |
| WO | WO9428809 | 12/1994 |
| WO | WO 9604860 A1 | 2/1996 |
| WO | WO9618349 | 6/1996 |
| WO | WO 96/29946 | 10/1996 |
| WO | WO 96/39914 | 12/1996 |
| WO | WO 97/06739 | 2/1997 |
| WO | WO 97/06740 | 2/1997 |
| WO | WO 97/06855 | 2/1997 |
| WO | WO 97/17029 | 5/1997 |

OTHER PUBLICATIONS

E.R. Cosman, et al., "Radiofrequency Lesion Generation and its Effect on Tissue Impedence", *Applied Neurophysiology*, 51:230–242, 1988.

*Modern Control Engineering*, by K. Ogata, Prentice–Hall, Englewood Cliffs, N.J., 1970.

E. Alexander et al., *J. Neurosurg.*, 83:271, 276, 1995.

Goldberg, et al., "Tissue Ablation with Radiofrequency: Effective Probe Size, Gauge, Duration and Temperature and Lesion Volume", *Acad Radio*, 1995, vol. 2, No. 5, pp. 399–404.

Melvin A. Astrahan, "A Localized Current Field Hyperthermia System for Use with 192–Iridium Interstitial Implants", *Medical Physics*, 9 (3), May/Jun. 1982.

Anderson, Gary et al., "A numerical study of rapid heating for high temperature radio frequency hyperthermia", International Journal of Bio–Medical Computing, 35 (1994) 297–307.

* cited by examiner

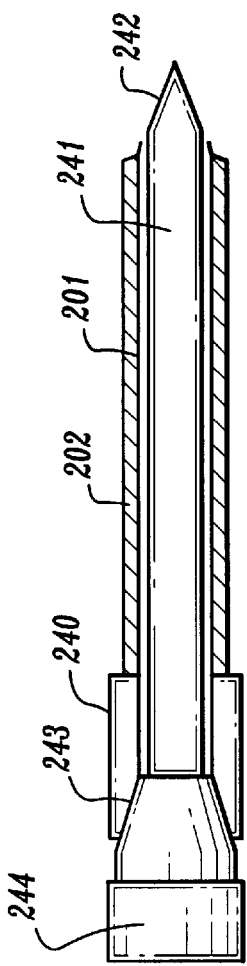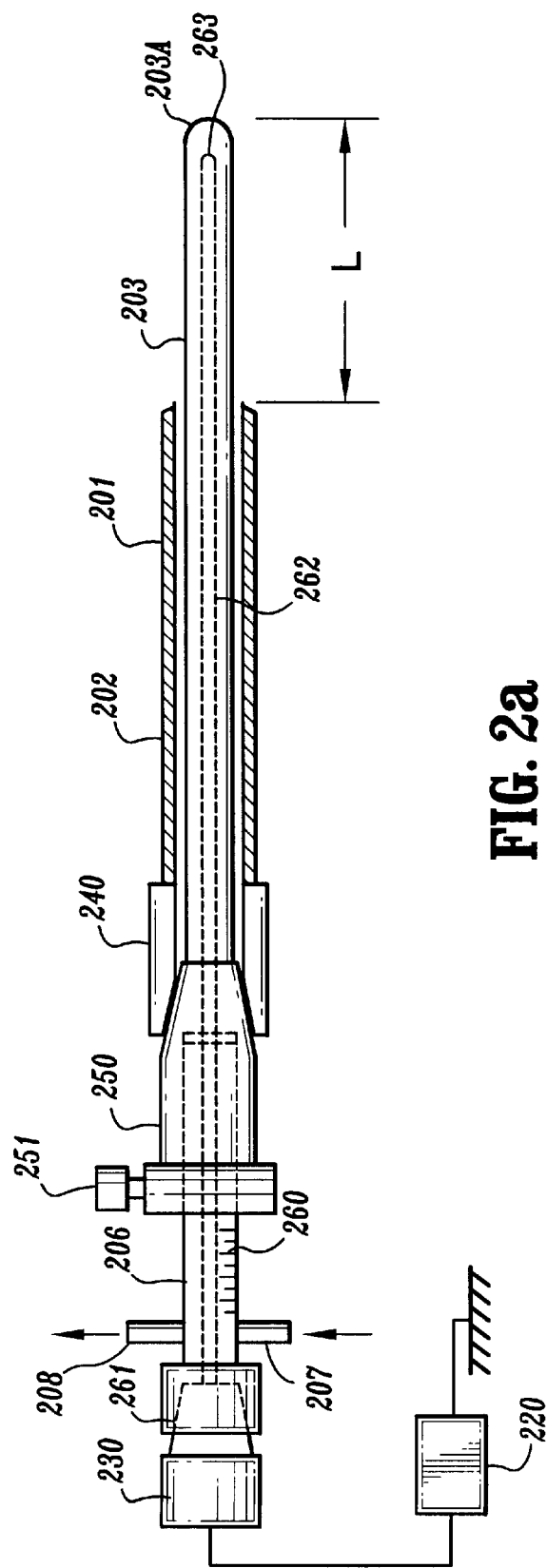
FIG. 2b
FIG. 2a

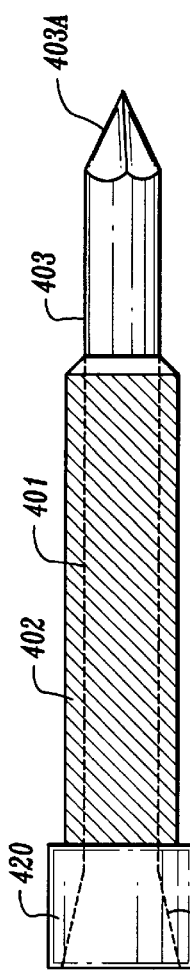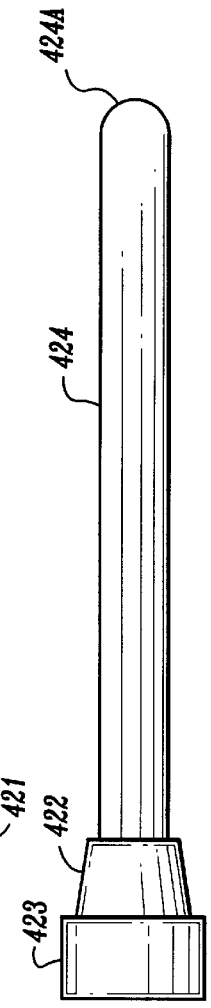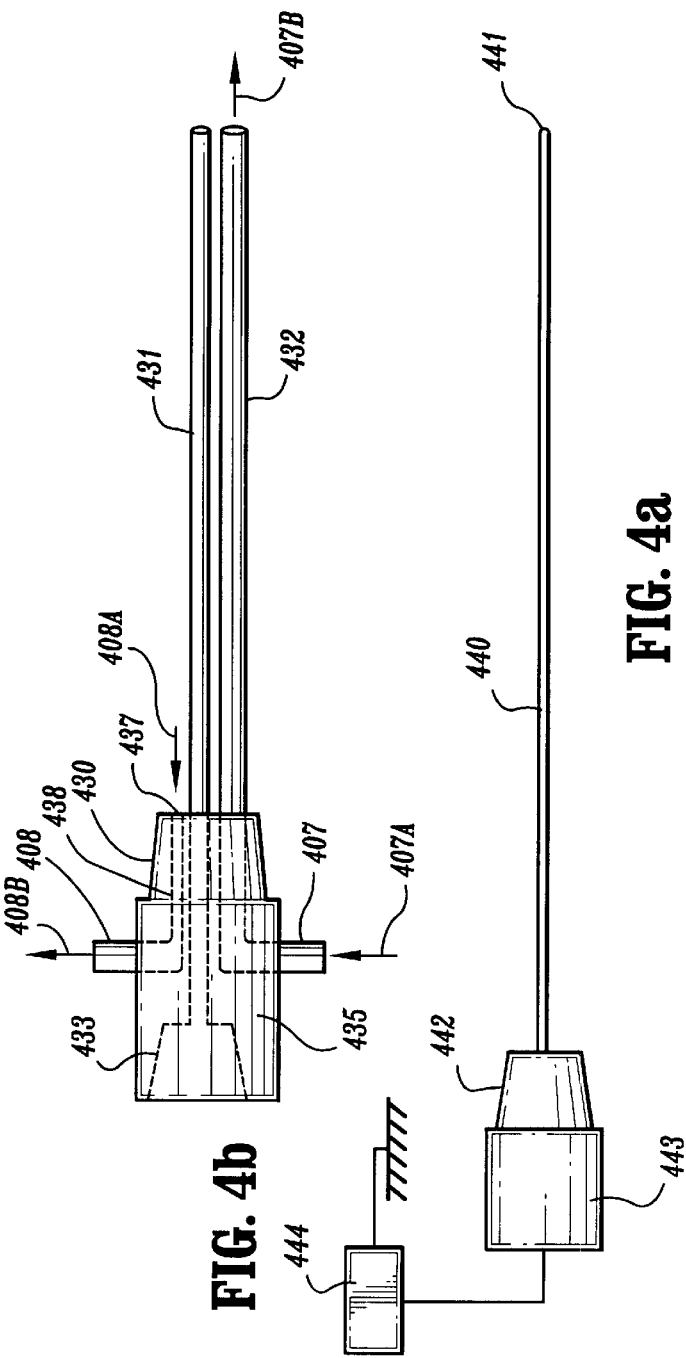
FIG. 4d
FIG. 4c
FIG. 4b
FIG. 4a

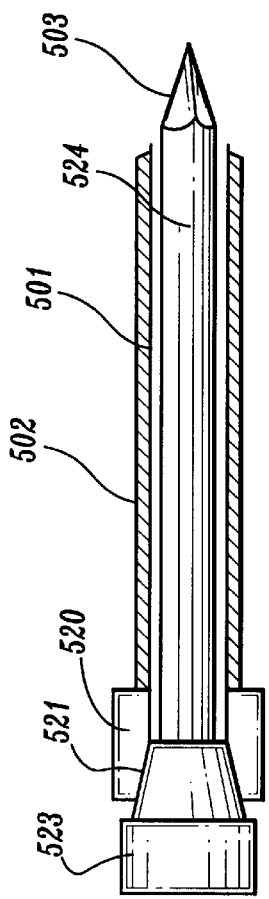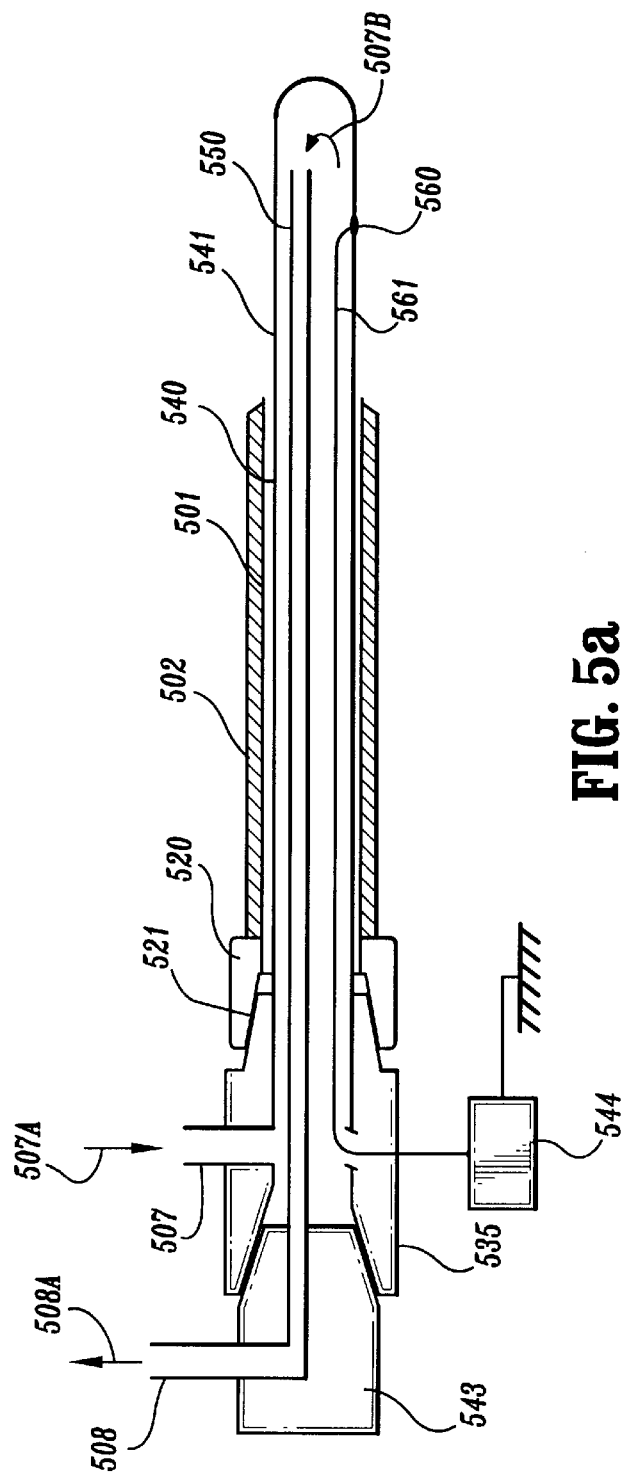

COOL-TIP RADIOFREQUENCY THERMOSURGERY ELECTRODE SYSTEM FOR TUMOR ABLATION

CROSS-REFERENCE TO RELATED APPLICATION

The present application is a continuation of application Ser. No. 08/562,986, filed Nov. 24, 1995, now abandoned, which is a continuation-in-part of application Ser. No. 08/433,799 filed May 4, 1995 now abandoned by William J. Rittman, III and Eric R. Cosman for "A Cooled Radio Frequency Electrode System for Heat Ablation in the Body."

BACKGROUND TO THE INVENTION

In the original parent patent application by the same authors, for which this is a continuation-in-part patent application, apparatus and method were described which included high frequency electrodes that are to be connected to a high frequency power source to heat bodily tissue when the electrode is inserted into the tissue, in conjugation with a cooling system which enables cooling of the electrode and the tissue just adjacent to the electrode so as to modify the thermal distribution of heat deposition in the tissue. Also described in the parent application were methods and apparatus for ablation of cancerous tumors by insertion of stiff electrodes into the body and creating an appropriately controlled lesion to engulf the tumor. Various configurations of electrodes and active, inactive, and boundary condition electrodes were shown for various geometric configurations in the body. Description of a complete control system integrated for controlling the temperature and power and other parameters associated with the heating and the cooling system were described, and the integration with the electrode system and patient related applicators with thermal sensing was detailed.

In the present continuation-in-part, we describe further designs of cooled-tip, high frequency electrodes well suited for percutaneous minimal invasive ablation of tumors or other structures within the tissue of the body. Specific apparatus embodiments are described that would be utilitarian in the thermo-surgical setting and which have physical characteristics to improve control and practical handling. Particular assemblies of cannulae, fluid cooling, irrigating and perfusion devices, radiofrequency cannulae, and thermal probes are given which make it possible to construct such a practical thermo-surgical applicator while preserving the integrity of control measurements, proper fluid seal joints, proper cleaning and flushing characteristics.

Further objectives of the present continuation-in-part is to describe cooled tip high frequency ablation electrode systems that are advantageous for ablation of cancerous tumors by percutaneous or intraoperative sticking of the electrode through the patient's skin or tissue so as to achieve the site of the tumor volume and practically ablate it.

Yet another objective of the present continuation-in-part is to show practical ways of constructing a thermo-surgical probe which is amenable to separability of function, cleaning and storing characteristics, manufacturer, disposability of certain parts, compatibility with imaging techniques during application, faithful temperature monitoring for control of lesion size, safety against degradation, damage, and transmission of disease, and other important functional characteristics, usable for cool-tip or non-cooled RF or other electrodes or probes.

A further object of this continuation-in-part is to describe various embodiments of control systems together with computer or computer graphic workstation devices to practically control the process of thermal ablation, to preplan the ablation using image scan data, to monitor the progress of the ablation with computer graphics, to regulate those parameters to which the lesion or ablation volume is sensitive, to provide controls for automatic handling of the ablation procedure, and to provide the appropriate preplanning parameters and parameter and image characteristic monitoring to assure desired ablation volume. These are claimed for use with a cooled RF electrode for a standard non-cooled electrode.

Another objective of the present invention is to provide a closed distal tip cannula or catheter with an open lumen other end (proximal) which can act as an electrode, and in various embodiments may accept a stiff stylet, or an RF connection element, or a cooling element, or combinations of these, so that such a cannula will reduce the spread of disease or cancer in its application, so that it may be made to penetrate tissue that is closed to coolant perfusion and flow, so that it is separable from more expensive RF coolant and other elements, and so it can be supplied in varying degrees of exposed or heating tip configurations.

It is another object of the present invention to provide separable cannula or catheter, RF element, coolant elements, temperature-sensing element(s), stylets, etc. so that any combination of such elements may be used together or separately or in pairs. For instance, a cannula may be used with an RF connection element only if ablation is done just using RF generator parameters to do thermosurgery (for example without cooling the tip or without temperature monitoring of any kind). Or, the cannula or catheter may be used with an RF connector and cooling element, but no temperature monitoring is done, and the ablation is carried out based on, for instance, control of the RF power or current delivered to the electrode, and possibly the temperature of the coolant fluid supply.

A further object of the invention is to provide an integrated system of RF (or other power type) generator and coolant supply system which can be connected to a probe, electrode, cannula, or catheter to enable easy, safe, convenient, and visible integration of control of the thermosurgery by the operator. We claim, for instance, an integrated console or workstation of these elements to be cooperatively connected to a probe or multiple probes, serially or sequentially, or in parallel to achieve a desired ablation (lesion) volume.

Yet another objective of this invention is to provide a system of RF generator (or other heating generator) with a computer to control, monitor, or feed back parameters of the thermosurgery, or to preplan the ablation, or to map, fuse, or update images from one or more image scanners before, during, or after the thermosurgery or ablation process, alternatively in another embodiment to control, monitor, feed back a cooling supply and flow to a cooled electrode(s) or boundary controlling elements which will be illustrated in the Figures below.

DESCRIPTION OF THE FIGURES

FIGS. 2a and 2b show a thermal ablation electrode system in section and partial section views which comprises an open lumen insulated cannula (in section view) with pointed insertion stylet, the stylet being removable, and an adjustable length radiofrequency electrode system in side view which can be inserted into the cannula with a closed end, and a third thermo-sensing/radiofrequency application probe which can be inserted into the radiofrequency cannula.

FIGS. 4a, 4b, 4c, and 4d show a set or system of components in side view for a radiofrequency ablation system comprising a closed, pointed tipped, insulated cannula with stiff solid stylet for insertion into the body, a second fluid-flowing coolant cannula having inflow and outflow channels at the hub and a fluid flow channel to deliver fluid to the distal-most portion within the insulated cannula, and a radiofrequency and/or thermo-sensing probe which can be inserted into the fluid coolant cannula, the entire assembly being separable and re-assemblable for surgery.

FIGS. 5a and 5b show yet another variation of the present invention in side sectional view which comprises an open lumen, insulated insertion cannula with pointed solid stylet for insertion into the body; a second radiofrequency electrode cannula with thermo-sensing and radiofrequency connections plus a fluid input connection; and a third fluid-carrying cannula which can be inserted into the second cannula for return flow of fluid which is circulating through the second cannula.

DESCRIPTION OF THE INVENTION

The present continuation-in-part relates to descriptions of the embodiments having to do with the parent invention and patent application of the present authors (U.S. patent application Ser. No. 08/433,799, May 4, 1995). The various illustrations described in the text and the associated figures are specific examples of advantageous or preferred embodiments which have particular practicalities and novelty for specific thermo-surgical or tumor ablation usage. It is understood that those skilled in the art can make further extrapolations from the general concepts of the parent application as well as this continuation-in-part, and that what is claimed here is intended to cover all such variations.

Figure 1:
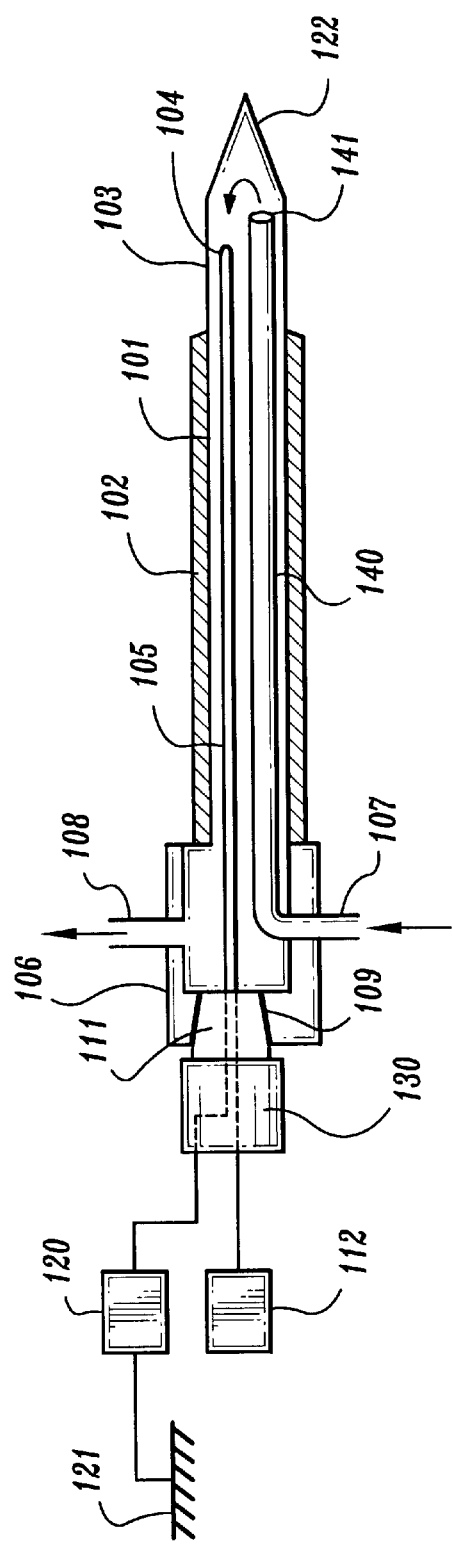
FIG. 1 shows a cooled tip thermal ablation electrode in section view with a closed, pointed tipped cannula which has coolant fluid inflow and outflow channels, and a separate radiofrequency connection and thermo-sensing probe which can be inserted into the cannula during thermo-surgery.

Referring to FIG. 1, an embodiment of the cooled tip radiofrequency heat ablation electrode is shown involving a cannula 101 which is elongated and can be inserted into the tissue of the patient, either percutaneously or intraoperatively, for instance into an open wound site. It has a closed, pointed tip 103 and 122 which aids in penetration of the tissue upon pushing the shaft 101. The shaft has an insulative coating 102 over a portion of its area and an unexposed distal tip portion 103. The exposed tip, when in contact with target tissue within the body and when connected to a high frequency generator, as described in the parent application, will give rise to high frequency currents emanating from the exposed tip into the surrounding tissue, and this in turn will give rise to frictional heating or high frequency power deposited in the tissue to cause heating of the tissue in the surrounding volume near the exposed tip 103. Such a high frequency heating circuit and heating mechanism has been described in the parent patent application and also in: (1) the article by Cosman et al., entitled "Theoretical Aspects of Radiofrequency Lesions in the Dorsal Root Entry Zone," Neurosurgery 15:945–950, 1984, and (2) Cosman E R, and Cosman B J: "Methods of Making Nervous System Lesions," in Williams R H, Rengachary S S (eds): Neurosurgery. New York: McGraw-Hill, Vol. III, pp 2490–2498, 1984. The pointed cannula system further has a hub 106 with inlet tubes or channels 107 and 108. Coolant fluid can be injected into or forced into, under pressure, the opening 107 and further along the internal channel 140 so as to emanate from the lumen 141 which is within the tip 103. The coolant fluid can then circulate back up the shaft, as indicated by the arrow within the tip 103 and flow out from the exit port 108 in the hub 106. Thus, this cooled tip electrode system in this embodiment has a closed construction and an internalized coolant circulation volume with input and exit ports for coolant fluid flow as indicated by the arrows in FIG. 1. The flow of the fluid could be reversed, and the input port could be considered to be 108, and the exit port considered to be 107. In FIG. 1, the hub 106 has a proximal connector known as a luer connector, which is a tapered hole 109. Into that female luer hole, the hub of a high frequency or thermo-sensing probe 130 can be inserted and sealed by its male luer configuration 111. The thermo probe has a shaft 105 which ends in the region of its distal end 104, and within the tip 104 there could be a thermal sensor which can sense the temperature of the coolant fluid at that point or, alternatively, could sense the temperature of the tip 103. Since the tip 103 is contiguous and in contact on its external side with the target tissue within the patient's body, the temperature sensor at point 104 can give a measure of the coolant fluid and, depending on the thermal contact with the wall 103, can get a measure of the temperature of the tissue immediately outside of the tip 103. Connected to or within the hub of the high frequency and/or thermal-sensing electrode 130 there are connections indicated by the dashed lines which connect to a high frequency generator 120 and/or a thermal-sensing circuit 112 that may be outside the body. The high frequency generator can be the source of high frequency voltage which produces the high frequency current that emanates from the tip of the cannula 103. For example, it may be a radiofrequency RF generator source similar to the RFG-3C RF Lesion Generator System of Radionics, Inc., Burlington, Mass. The temperature-measuring circuit 112 could be of a thermocouple type, and the temperature sensor could also be a bi-metal junction thermocouple such as copper constantan. This type of temperature sensing has been known in the state of the art for decades and is illustrated by the TC thermocouple radiofrequency electrodes of the Radionics, Inc., Burlington, Mass.

An advantage of the configuration of FIG. 1 is that the cannula 101 could be a disposable cannula or a non-disposable cannula, and it houses the thermal circulation system in an intact, closed-ended, tissue-penetrating structure. Since the high frequency/thermo-sensing probe 105 can be removed from it, any failures of the high frequency or thermo-sensing device will not compromise the usage of the cannula 103 and vice versa. This modulization or compartmentalization of the functions represented by the cannula and the high frequency structure enables separate reusability or disposability of each of these elements in the surgical setting. The cannula 101 may be of tubular construction and may be made from a variety of materials including plastics, metals (such as stainless steel, titanium, non-magnetic alloys), or conducting composite materials. The insulation 102 can be made from a variety of satisfactory types such as Teflon, polyethylene, etc., and these are illustrated by the electrode designs of Radionics, Inc., Burlington, Mass. The hub 106 can be made of metal or can be made of plastic. A plastic hub is amenable to low artifact imaging by X-rays. The input ports 107 and 108 could be simple corrugated, rigid ports, or they may be flexible tubular coupling to minimize torque transmission to the electrode during usage. Tubular coupling could include PVC tubing with plastic luer connectors on the end for easy connection to the hydraulics of the cooling fluid system.

FIG. 2 shows another embodiment of the invention which comprises a set of instruments of different configuration from that of FIG. 1. In the upper portion of FIG. 2, there is shown an open cannula 201 with insulation over a portion of its surface 202. The cannula has an open lumen at its far (distal) end. It has a hub 240 which may be metal or plastic—plastic or a low radiopacity material being desirable for position confirmation by X-ray, CT, or MRI scans. The stylet shaft 241 occludes the cannula lumen and has a pointed tip 242, which may be a trocar, conical, bevel, or other shape for easy penetration of tissue when the cannula and its stylet are introduced into the patient's body. The tapered (luer) hub 244 of the stylet secures, locks, and/or seals to the female luer tapered hub 240 of the cannula 201 in the usual fashion.

Once the cannula and stylet have been introduced into the tissue to the appropriate place near the target volume, the stylet can be removed and an RF/coolant cannula 203 can be introduced into the cannula 201. This is shown in the lower portion of FIG. 2. There is a sizing clamp 250, with locking screw 251 which mates to the luer taper of hub 240 and secures to it. The cannula 203 can be slid to greater or lesser depth within the sizing clamp 250 so that the length L of extension of the tip 203 of the RF/coolant cannula can be made greater or lesser accordingly. A measure of the degree of extension L could be indicated to the operator by the scale markings 260 on the hub portion 206 of the RF/coolant cannula 203. The RF/coolant cannula may have an exposed conductive tip 203 which extends beyond the insulated shaft of cannula 201 such that when an electrical high frequency connection is made to the cannula 203 via a connection means in its hub portion 206, then high frequency current will emanate into surrounding tissue from the exposed tip 203, thereby heating tissue in the environment of the exposed tip 203. The size or length of the lesion or ablation volume so made will vary according to the degree of extension L. Thus the tip length L may be varied beforehand by the operator to gauge the length of the ablation volume that is desired from the thermo-surgery. Connection tubes 207 and 208 serve as the in-flow and exit ports for coolant fluid that is passed into the interior of the cannula 203 in the tip region of the cannula so as to cool the tip or "clamp" it to a desired temperature. This in turn cools the surrounding tissue near the tip, thus "throwing" the temperature distribution outward, away from the tip so as to achieve a larger ablation volume. This novel aspect of the invention has been described in the parent application. Furthermore in FIG. 2, there is RF/thermo-sensing probe 262 which is inserted into RF/coolant cannula 203. Its hub 230 secures, in this example, by a luer lock 261 to the hub 206 of cannula 203. The RF/thermo-sensing probe 262 in this example is shown connected to an external source of high frequency (viz., RF) power 220. This high frequency generator then supplies high frequency voltage to the connections in hub 230, and thus to the element 262, which may be in contact through the hub or in the cannula region to the RF/coolant cannula 203, thereby raising the high frequency potential of the exposed tip 203 to achieve heating in the nearby tissue. Furthermore, in the tip 263 of RF/thermo-sensing probe 262, there may be a thermocouple or other type of temperature sensor which can sense the temperature of the coolant fluid or (if configured to touch the inner surface of the tip 203) to detect the temperature of the tip itself which approximates the temperature of the tissue surrounding the exposed tip 203. The RF/coolant cannula 203 has a closed hemispherical tip 203A in this example. This means that the coolant has a closed chamber in which to flow. In this example, after the pointed stylet 242 has been removed, the RF/coolant cannula 203 when passing through the outer cannula 201 can push further into the tissue. Alternatively, the cannula 201 can be withdrawn back over the RF/coolant cannula 203 so as to expose the tip 203 in the tumor volume. The cannula 203 may have a sharpened point as an alternative to the rounded full radius point 203A shown in FIG. 2.

Figure 3:
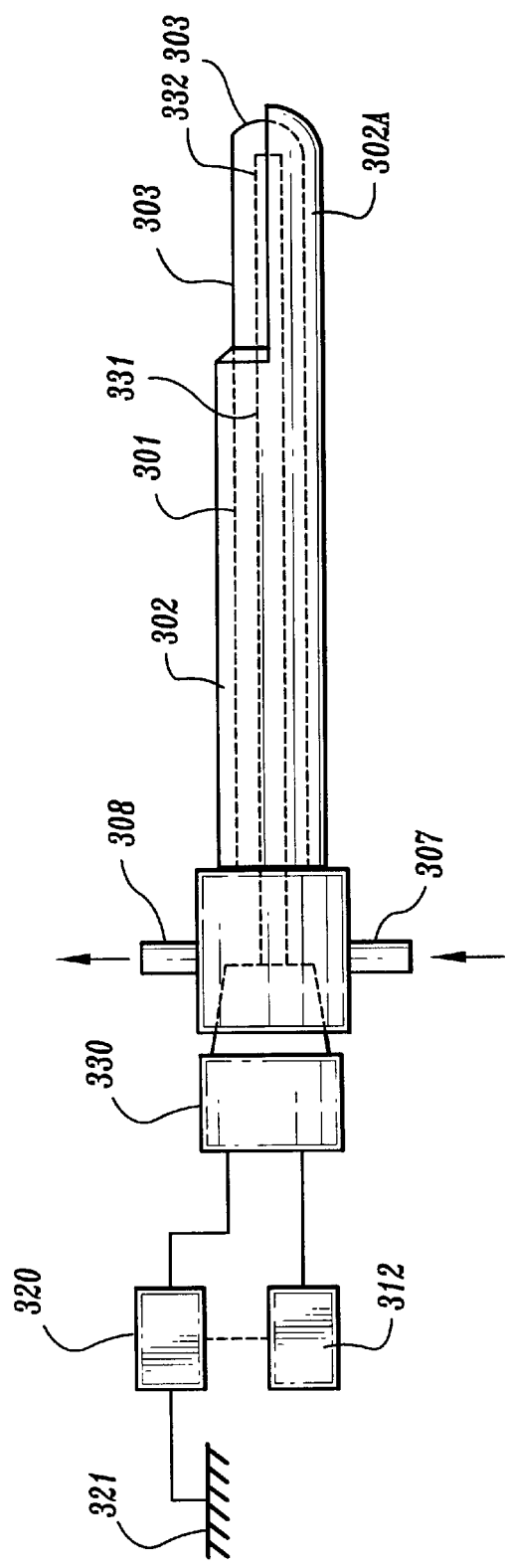
FIG. 3 shows a radiofrequency ablation probe in side view which has a "windowed" tip, including an exposed tip surface which is located on only one side surface of the electrode shaft.

FIG. 3 shows another embodiment of the present invention in which the cannula 301 has insulated portion 302, but has a "window" of exposed conductive surface area at its distal end. The exposed conductive surface 303 is shown on one side of the cannula, whereas on the back side of the tip there is insulation 302A which prevents high frequency current from emanating from the back side. Thus there is a directionality of the high frequency current emanating into the tissue, and thus a directionality of the heating process accordingly. The tissue will therefore be heated up on the "window" side of the exposed tip, but not on the opposite insulated side in the proximity to the tip. This provides the possibility of making non-symmetrical lesions or azimuthally asymmetric lesions in tissue and the possibility of extending the ablation volume laterally in a given direction from the high frequency electrode tip, but not in an opposite direction. In this example, the hub has in-flow and out-flow tubes 307 and 308 and a radiofrequency connection means through hub 330 of an RF probe 331 which is inserted in the outer cannula 301 during the RF ablation process. The RF element 331 may contain connections for high frequency current carrying as well as thermo-sensing in its tip 332. The thermo-sensing technique referred to here, as in all of the examples described in this application, may comprise multiple thermo-sensors which can be distributed longitudinally or azimuthally on the electrode shaft or tip and can be used to detect the temperature at various points in or around the exposed tip 303. For example, there may be one sensor to sense the temperature of the coolant fluid by being in the main flow stream of the fluid, whereas another sensor may be pressed against the wall or connected to the wall of the cannula window 303 itself so as to measure more exactly the temperature of the wall of the electrode and therefore of the tissue immediately outside the electrode. In this way, a great deal of flexibility can be achieved in monitoring the status of the coolant and the heating process as the high frequency ablation proceeds, all this data may be used by a control or feedback system to govern the RF and coolant supplies.

FIG. 4 shows yet another embodiment, in side view, of the present invention with a different and useful implementation of the various elements involved. In the topmost portion of FIG. 4 there is shown a closed, pointed, and partially insulated cannula 401, with insulation 402 over a portion of its elongated length. The exposed tip 403, as before, is the conductive surface through which high frequency current can pass to the tissue. In this example, a trocar or other beveled point 403 would enable penetration or self-penetration of the cannula into tissue of the patient to achieve the target volume or target tissue location. The hub 420 may be metal, plastic, or other material, and has a female luer shape 421 on its inner diameter for locking subsequent elements. The next element, shown second from the top in FIG. 4, is a stylet 424 which can be inserted into the sharpened cannula 401 at the time of insertion of the cannula into the body, and its hub 423 has a male luer shape 422 which matches with the female luer shape 421, and thus secures to it. The stylet 424 within cannula 401 will then provide a stiffer structure for forceful manipulation of the electrode or penetration and pushing of the electrode into the bodily tissues.

The next element in FIG. 4 is the coolant cannula represented by the elongated structure 432 which has an opening therethrough and connects to an inflow element 407. The cannula also has a hub 435 with male luer shape 430 such that the entire assembly can be inserted into the cannula 410 at or about the time of heat ablation. The hub structure 435 has a channel 438 within it and an opening 437 at the front surface of the luer hub structure which communicates with the inner space between the coolant cannula 432 and the interior of insertion cannula 401 when the coolant cannula is inserted into the outer cannula. In this way, fluid which is injected through the input port 407, as indicated by the arrow 407A, can return flow by emanating out of the distal lumen as shown by the arrow 407B and return back via the direction of the arrow 408A through the internal channel 438 and out the exit port 408, as indicated by the arrow 408B. Also shown in the coolant cannula is a luer opening 433. This matches to the male luer surface 442 of the RF cannula shown at the bottom-most figure in FIG. 4. The RF cannula has an elongated element 440 which can be inserted into the channel 431 of the coolant cannula so that the tip end 441 is at the distal tip end of 431 or even at the most distal tip-interior region of tip 403. Tip 441 may contain a thermo-sensor to detect the coolant fluid temperature, or it may be adapted to contact intimately the wall of tip 403 so as to detect the tissue temperature nearby. Hub 443 has a luer lock 442 to seal or electrically connect to female luer hole 433 of the coolant cannula. The RF cannula connects to an external RF generator 444 to provide RF power via the RF cannula to the outer cannula 403, and thus to cause tissue heating during thermo-ablation.

The system of FIG. 4 can be embodied in a more simple way. For instance, one may have only the cannula 401 with its uninsulated tip 403 and possibly the insulated portion 402. If it is stiff enough, you do not need stylet 424 for penetration of tissue. Probe 432 may have only one channel such as 432 for fluid circulation and no channel 431; i.e. it could simply have a male luer hub 430 with a single tube to insert into cannula proximal open end 420, and have a fluid connection to a coolant fluid supply, such as a syringe of cool saline water. An exit fluid port, vent, or tube may be present either on the hub 435 (such as 408) or on the proximal hub 420 of outer cannula 401. Electrical connection to the cannula 401, and/or to the tip 403, could be made by an "alligator" or push-on pin connector on hub 420 or hub 435. Also claimed herein is the embodiment where such outer cannula and inner probe are permanently sealed or bonded together at the factory as one integral unit.

Referring to FIG. 5, another embodiment of the present invention is shown, in section view, which has its own specific features and advantages. In the upper portion of FIG. 5, a cannula 501 is shown which has an open front end or distal end. It is insulated over a substantial portion of its surface area with insulation 502, as in the above examples. The stylet 524 is inserted into the cannula 501, and the stylet has a pointed tip 503 for penetration of tissue. Thus, when the stylet 524 is inserted to its hilt, represented by the luer portion 521 of its hub 523 into the cannula 501, the assembly can be inserted conveniently into the patient's body, and the tip region 503 can approximate the target tissue volume. At this point, the stylet 524 may be removed, and a coolant/RF cannula, represented by cannula 540 in the lower portion of FIG. 5, can be inserted into the same cannula 501 such that the exposed tip (or distal) end 541 of the coolant/RF cannula emerges from the distal open lumen of cannula 501 so as to represent the high frequency conductive portion of the electrode with respect to the bodily tissue. In this example, the coolant/RF cannula 540 has a hub structure 535 which has an in-port 507 for coolant fluid, as indicated by the flow arrow 507A. The hub 535 seals to the cannula hub 520 by the luer taper lock 521. Also shown in cooperative connection to the coolant/RF cannula is the connection means to the RF or high frequency generator 544 external to the body. This connection means can take the form of a standard cable connector or a leader wire or a jack-type contact or other designs known in the high frequency engineering art. The temperature-sensing and/or radiofrequency electrical connection can be made schematically by the element 561, which runs to the tip region 541 and is connected there by element 560. This may be a weld, braze, or other type of secure electrical connection. If the thermo-sensor is a thermistor, or a thermocouple, or other type of sensor, it can be fused at the junction 560 so that it is reading the temperature of the wall of the tip 541 at its external surface or intimately on a thin wall surface of the tip 541 so as to give an excellent representation of the temperature of the tissue immediately outside and adjacent to the tip. The temperature sensor may be elsewhere and substantially inside of the volume of the tip and at various locations so as, for example, to measure the temperature distribution inside or at the surface of the tip 541 at different locations, either longitudinally or azimuthally. It may also measure the temperature of the coolant fluid at different positions along the flow path of the fluid so as to monitor the amount of power sinking into the fluid from the heating process in the tissue outside the tip as the heat convects or conducts back into the tip 541. A third cannula element is shown by the structure 550 which may be tubular in nature and connect back to a proximal hub 543 that is connected again by a luer connection or lock to the hub 535 of the RF/coolant cannula. This third structure may be a fluid return inflow device having an inflow or alternatively an outflow port 508 in FIG. 5, the arrow 508A showing outflow of fluid in this example. It could equally well be inflow, and thus the flow be reversed in direction. The outflow would the arise from inflow via port 507 down the RF coolant cannula 541 to the distal tip, where the flow indicated by the arrow 507B returns back up the outflow fluid channel 550 and then emanates from 508 according to the arrow 508A. The third structure 550 and its hub 543 may in fact have both inflow and outflow ports together in that one structure. Note also, that various locks or fluid sealing elements may be used rather than the luer locks used in the examples in FIGS. 1, 2, 3, 4, 5, and 10, as such locks or seals are known to those skilled in the art.

The system of FIG. 5, then, shows an example of a three-element cooled tip electrode structure with an open cannula with stylet that could be disposable, a disposable or non-disposable RF coolant cannula with indwelling thermometry and high frequency connection wires or other means, but also having part of the coolant flow channel and passages within it, and a third structure, which may be disposable or non-disposable, being the remaining flow element indicated by the tubular cannula element 550 and other connected hub and fluid flow ports.

The embodiments of FIGS. 1, 2, 3, 4, and 5 each have operational advantages in the clinical setting. There are further variations of these designs and details which could be devised by those skilled in the art. Without limitation, a few of these clinical advantages of the examples in FIGS. 1, 2, 3, will be mentioned here.

In FIG. 1, the insulated cannula 101 could be disposable or non-disposable, with a plastic radiolucent hub 106 and sharpened point 122. The RF and thermometry element 105, which may tend to be expensive and electronic in nature may be separable. The separability of the two elements means that spare pieces can be present in the event of failure or interchangeability of these elements is possible, one to the other, and storage and cleaning is safer.

In the embodiment of FIG. 2, the insulated cannula 201, with its pointed stylet, is easy to prepare and can also be disposable or non-disposable. It has, therefore, the feature that it can be thrown away or separated from the rest of the more complicated parts. For example, if multiple cannula tracks are to be placed in a target volume, multiple such relatively simply constructed cannulae and stylet systems can be implanted, and one after another the coolant, RF, and thermometry devices can be inserted. The embodiment of FIG. 2 has the advantage of an open lumen insertion cannula 201 with obdurating stylet 241, which is particularly easy to construct. This could be a disposable element. Both cannula and stylet could have radiolucent plastic hubs, for example, which make it ideal for CT, X-ray, angiographic, or other scanning techniques. In all of the designs described in this continuation-in-part, as in the previous parent application, the use of MRI-compatible materials (viz., with low magnetic permeabilities relative to, say, steel) could be helpful so that if intraoperative pre-ablation, ablation-contemporaneous, or post-ablation scan studies are done in the MRI magnetic resonance imaging machine, that perturbations of the image from such MRI scanning will be reduced or eliminated to highly permeable or magnetic materials. Such materials as titanium or very low iron, high cobalt nickel alloys (viz., Inconel), or even plastics or carbon fiber can be used in this application. The use of the cannula of the irrigation or fluid perfusion cannula 203 with its sizing hub 250 is convenient since the separability of this relatively more complicated element means that it can be used interchangeably with the outer cannula 201 or can be used as a non-disposabe element and easily cleaned between cases. The further advantage of being able to size the length of the tip L means that the clinician can preplan for a given tumor size (viz., determined by pre-ablation images), and insert the coolant cannula to extend beyond the cannula 201 tip for the appropriate penetration and coverage of the target tissue and to make a lesion or ablation volume appropriate to engulf the entire tumor volume or other target structure volume. Further, the separable element 262, which is the RF/thermometric device, is also conveniently configured. This device may be non-disposable and more elaborate than the other components. Thus, it can be reused for different thermosurgical episodes, or if several cannulae such as 201 are placed with coolant cannulae 203, the RF thermometric probe 262 can be inserted serially within these in the same patient, at the same interventive session, and sequential RF ablations can be performed. Another advantage of the construction in FIG. 2 is that the cooling irrigation elements and the RF elements are separate and can be separated and reassembled after thermosurgery, and therefore cleaning, sterilizing, and removal of surgical debris becomes easier.

With respect to the design of FIG. 2, the open cannula 201 may be disposable, and the RF coolant cannula 203 may be disposable or non-disposable. If it is non-disposable, it is then possible to easily clean the cannula 203 externally and by flushing out internal debris or ionic substances such as saline. It is noted that cooled or even ice-cold saline is a coolant fluid of advantage to be used here, and thus all traces of salt solution should be flushed away after use and before storage to prevent corrosion of the component parts. To be able to adjust the tip exposure L has the advantage that potentially, with one insertion cannula 201, a variety of lesion size lengths can be achieved. Furthermore, the separability of the RF/thermometric element 262 makes it possible that this potentially expensive and delicate element can be held as non-disposable and less perishable by having it as a separable and cleanable element.

The design of FIG. 3 has the advantage that the radiofrequency current and the heat deposition can be sent out into the tissue directionally or selectively in a given direction with respect to the tip of the insertion cannula 301. This makes possible selective thermo-surgery with angular variability. For irregular shaped tumors or structures, this may be clinically important. Also, in the situation where a critical structure is near the tip, it is possible to shield it from heat emanation by facing the window 303 away from that critical structure.

Among the advantages of the embodiment in FIG. 4, the self-penetrating or pointed closed-end cannula 401 with its associated stylet 424 makes it possible that this element, whether disposable or non-disposable, is self-contained and is the only element which is exposed to the bodily tissue, the target structures which may be cancerous tumors or bodily fluids. Thus, in the effort to minimize transmission of disease from one patient to another, or indeed from one insertion tract to another in the same patient, this element could be, for example, disposable, or specially cleaned if non-disposable, to act as a mechanical barrier to the other electromechanical structures that are inserted inside it. Therefore, the cooling fluid element 432 and the RF thermometric element 444 will not be directly exposed and in contact with patient tissue, and thus there will be less risk of their producing contamination, and even spread of cancer, from one thermosurgery event to another. Furthermore, the fluid coolant element 432 and the RF thermo-measuring element 444 can be cleaned easily after a procedure by separating them from the cannula 401, giving full access to their complex structures. This separability means that they can be delicately stored and cared for, and make them, therefore, amenable to longer life and use in the non-disposable context.

With respect to the embodiment of FIG. 5, again it has the open cannula 501 with sharpened stylet 524, making it possible as a self-contained, potentially disposable unit to penetrate directly through the skin and tough tissue of a patient's body into a target volume such as a cancerous tumor deep within the body. Examples of these target volumes are in the liver, thorax, prostate, bone, head and neck, cranium, etc. Once in place, the RF coolant structure represented by elements connected to 541 and 550 can be placed down into the cannula 501 and on into the target volume. Thus, their role is less subject to abuse than for the cannula/stylet 501 and 503 on initial insertion. Again, because they can be separated, they can be easily cleaned and stored separately. By their potentially delicate nature, this will increase their surgical lifetime and their probability of reliable use. As mentioned above and in the parent application, there is a variety of possibilities of measuring the coolant fluid, internal and surface temperatures of the thermo-surgery probes including multiple thermo-sensing elements over the interior of the probes at varying locations to fully monitor the process of heating. In addition, side-emitting or satellite thermometric probes or cooling elements can be put into place or built in conjugation with such embodiments as was described in the parent application. In the example of FIG. 5, the placement of the thermo-sensor 560 at the very surface or near the surface of the power radiating element 541, whether it be microwave, radiofrequency, laser, or other type of heat deposition system, will enable a faithful, fast-acting, and accurate interrogation of temperature of the tissue just adjacent to the energy-sending tip 541. This would make it possible to have a much tighter control of the entire thermo-surgery process, as it is at the surface of the tip where an important thermal boundary condition is set. That is, by proper fluid cooling of the tip, the tip becomes thermally "clamped," and thus by knowing the corresponding power, current, energy, voltage, or other thermal-generating parameters from the external generator 544, a prediction control diagnosis or real-time monitoring of the process and the extent of the thermal ablation is then feasible and possible in practical terms. For instance, by setting the tip temperature at 30° C. by coolant flow and thermometry monitoring, it might be determined that in liver ablation delivery of P watts of RF power from a tip of L mm length and D diameter will produce an ablation volume of length l and diameter d having the shape of a prolate ellipsoid. Such a paradigm or similar practical procedures are claimed herein and in the parent application.

The coolant RF cannula 540 is a more elaborate structure and potentially more expensive than the cannula 501. Therefore, this may be, for example, non-disposable. Because of its physical separability, flushing, irrigation, and cleaning through the port 507 and out the exit tip 530 can be handled easily for this coolant RF cannula. Cleaning is very important, since the insertion into cancerous tissue may involve a very sick patient with potentially communicable diseases, and making it desirable to avoid any possibility of transmission of tumor cells, even within the same patient. Thus, sterility and cleansing of each element is paramount. The third element 530, again, is separable and cleanable so that, for example, if the coolant element is liquid saline solution, which has a corrosive character if left to stand, can be washed out, rinsed, and de-ionized between surgeries to maintain the integrity of each element. Thus, in the design of FIG. 5, a practical set of instruments could be: a disposable cannula stylet set 501 and 524 with, for example, non-disposable RF coolant cannulae 540 and a non-disposable irrigating cannula 530.

Thus, there are varying advantages and relative merits for the designs and embodiments of FIGS. 1 through 5, some of which have been elucidated and described in this continuation-in-part. Others skilled in the art can design variants of these examples and elaborate other advantages and functional features of such designs. All of these are intended to be covered by the parent application and this continuation-in-part. In the examples above and in the parent application, external elements such as 112 and 120 in FIG. 1, 220 in FIG. 2, 320 and 312 in FIG. 3, 444 in FIG. 4, 544 in FIG. 5, and similar elements in the parent patent application can be considered as complex control systems and delivery systems, both for heating power, coolant supply, control, and monitoring, feedback systems among these elements, computer graphic workstations to monitor previously taken, preplanned, or contemporaneous scanning data, monitors related to real-time monitoring or post- or pre-thermosurgery monitoring such as ultrasonic, sonic, angiographic, CT, MRI, PET, or other imaging and scanning or detecting means, algorithms built into such computer systems for prediction of thermal distribution, calculation of predicted or concurrent thermal-distributions, monitoring of thermal distributions, description or display of predicted, preplanned, or actually imaged isotherms or powertherms or other displays of lesioning or ablation parameters such as temperature, current, power, impedance, energy, tip geometry, etc. which are related to the overall thermo-surgery process. FIGS. 6, 7, 8, and 9 are examples or embodiments of such systems that may be used in conjunction with a thermo-surgery probe with cooling system which are useful and could be implemented to manage the overall ablation process.

Figure 6:
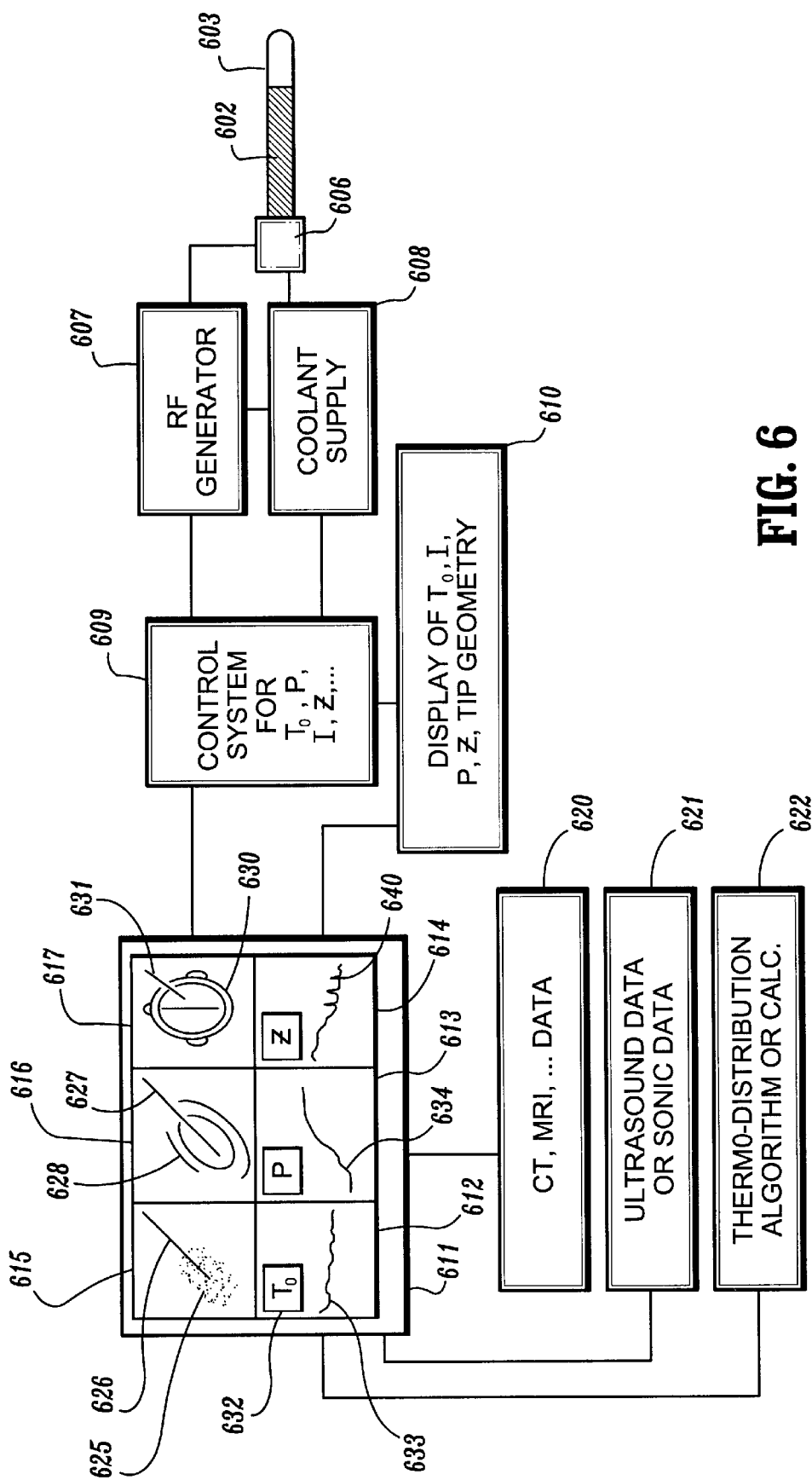
FIG. 6 shows the arrangement of a power and cooling control system connected to a high frequency, cooled tip electrode for controlling critical parameters of tip temperature, power input, impedance, etc., and displaying those parameters on a computer graphics screen, in some cases together with image scan data that can be used to preplan and/or real-time monitor the RF heating ablation.

Referring to FIG. 6, we take the example of a high frequency or RF thermo-ablation electrode to be placed in the body and having an insulated shaft 602 and an electrically exposed tip 603, this shaft and tip being adapted to be inserted into the body of the patient so that the tip 603 is near a target volume such as a cancerous tumor or other tissue structure within the body. The hub or junction connector element illustrated schematically by 606 may be the connection devices such as jacks, hoses, ports, etc. which connect the RF electrode to, for example, a power source such as the radiofrequency (RF) generator 607 and the coolant supply device 608. As described in the parent application, both of these elements 607 and 608 could be complex structures in and of themselves. For example, the RF generator 607 could be represented by a multi-parameter RF lesion generator, stimulator, impedance monitor, thermometric readout device such as the RFG-3C Lesion Generator System of Radionics, Inc. in Burlington, Mass. The coolant supply system 608 could consist of a complex system of fluid reservoir, pumping system, thermometry readout system, feedback and control system, reservoir input and output pressure control system for monitoring and safeguarding against overpressures, coolant fluid channel blockages, and other such untoward possibilities. These also may be coupled and fed back to the controls of the RF generator 607 so that the entire system 607 and 608 may be one integrated console unit system or concatenation of systems. Also shown is the control system 609, which schematically may be a computer, microprocessor, or electromechanical device that has input of the parameters from the RF generator 607 and/or parameters from the coolant supply system 608. For instance, the RF generator 607 may have readout of power, current, voltage, energy, time, impedance, and temperature from multiple temperature sensors in or around the thermal delivery tip 603, and the coolant supply system 608 may have readout of temperature, multiple temperatures at different points, flow, pressure, pressure differentials, and similar parameters related to the activity, delivery, temperature, pressure in and around the cooling fluid or cooling fluid delivery system, these parameters feeding into the control system 609 together with the parameters from the RF generator 607. These parameters can then be used as feedback control input parameters and the control system can deliver back to the generator 607 or supply 608 control parameters which modulate, moderate, or otherwise monitor their output response or course of action. The control system 609 may be the mediator for a preplan from, for example, a computer system illustrated by element 611, and thus element 609 may control the power parameters or the feedback readout parameters so as to govern the course of the heating or cooling process. Many examples exist in electrical and mechanical engineering of control systems. Examples of writings on feedback control systems are everywhere in the literature and could be illustrated by the textbook *Modern Control Engineering*, by K. Ogata, Prentice-Hall, Englewood Cliffs, N.J., 1970.

Also shown in FIG. 6 is schematic element 611, which might be, for example, a PC or computer graphic workstation. It may take the parameters of the RF generator 607 and coolant supply system 608 plus other geometric parameters regarding the electrode as well as image scan data taken before, during, or after thermo-surgery, assimilate all of these parameters, display them in various representations, slicings, time courses, reformattings, digital subtraction representations, graphical representations, digital representations, analog meter type representations as an interface to the operator or controller of the processor during the preplan process or during the process of ablation heating itself. To give a specific example of what this might entail, but in no way to limit the other possibilities of such display and control as could be thought of by those skilled in the art, the element 620 might represent an image scan machine or a computer processor of image scan data from such image scanners such as from CT, MRI, PET, or other tomographic or X-ray, plain film, or digitized image scan data. That data could be set into the computer system 611 and be represented as an array of raw data, slices, reconstructed slices, three-dimensional renderings, "slice and dice" three-dimensional or two-dimensional renderings, contoured or segmented anatomical structures; color-rendered, differentiated structures, both pathological and normal so that the surgeon may substantially visualize the anatomy and pathology of the patient prior to, during, or after the procedure. Data from CT or MRI may be taken days or even months prior, and could be put into stereotactic or non-stereotactic space by means of body localizers, immobilizers, fiducial marks, graphic reference means, etc. as is exemplified by the patent application of Russell Brown, U.S. Pat. No. 4,608,977, entitled "System Using Computed Tomography as for Selective Body Treatment, Sep. 2, 1986. The literature from Radionics, Inc. in Burlington, Mass., shows many other examples of input and indexing from stereotactic and non-stereotactic devices of such image scan data. Element 621 may represent ultrasound scan data or sonic monitoring data such as from a stethoscope or electronic microphone or sonic detector system which can visualize before, during, and after the thermo-surgery procedure the course of the electrode in the body, its position with respect to anatomy, and even the process of the heating mechanism and result thereof. This data could also be fed into the computer system 611 and represented in various ways alternatively on a graphics display screen. Furthermore, there may be calculation algorithms, look-up tables, heuristic algorithms, historical clinical data, mathematical calculations involving field and thermal distribution calculations by finite element methods, analytic form solutions, computer theoretic methods, etc. which can be used in a preplan setting and displayed, implemented, overlaid, and used to control the image data, course of RF generator output and coolant supply as well as the control system to tailor or preplan the results of the thermo-surgery that can be visualized again on the computer graphic workstation 611 and indeed computed and stored within that same computer 611. Some illustrative examples useful displays from such inputs are shown schematically in FIG. 6 as well. In the window 615 on the graphics display, one might see the real-time or preplanned trajectory of a probe path 626 and electrode tip as it makes its course into the body to a tumor structure represented by the cloud of dots. This might also be, for example, the display from an ultrasonic, CT, or MRI scanner which actually visualizes the probe 626 and a tumor 625 or a profused volume corresponding to the destructive ablation volume, perhaps represented or visualizable as volume 625. It has been determined by the present authors that use of CT contrast agents can be used to "see" the ablation volume following thermosurgery, and this can give a direct view of the results immediately following the heating process. In window 616, there may be shown a preplanned path of an electrode 627 in a particular slice or reconstructed slice plane of volumetric rendering in a three-dimensional aspect, and also shown isotherm surfaces or intersected surfaces or isotherm lines represented by 628, which might represent a preplan or a calculation of the thermal distribution and ablation volume around the tip of the electrode 627. In the window 617, a view, slice, reconstructed slice, of three-dimensional rendering 630 of the patient's anatomy might be shown, and within it a preplanned or actual plan or post-thermosurgery path 631 representing the approach of a thermosurgical probe such as 602 into the patient's anatomy to achieve a target volume which might be seen on that image slice such as for example a tumor as seen on CT, MRI, angiographic, or other types of image scan data. In these representations, multiple electrode paths may be shown parallel, non-parallel, stereotactically placed, or in various locations within the body and also indifferent reference electrodes shown with possible boundary condition cooling electrodes such as was described in the parent application and further described below. In the display window 612 is shown a graph in time, or frozen in time, or preplanned representing, for example, the thermosensor readout of one or more temperature sensors associated with the coolant fluid, RF heating electrode, tissue around the heated electrode, tissue within the body, the reference electrode, temperature at various points within the electrode tip, temperatures within the cooling supply system, etc. A digital display or multiple digital display of these temperatures might be shown in a sub-window 632. A graphical readout as a function of time could be displayed as a curve 633 representing one or more of the temperature readouts mentioned above. The temperature readouts could be differentiated by time sequence displays, color-coded displays, variations in the texture or nature of the displays themselves. A red curve might represent the tissue temperature, for example; a green curve could represent the temperature of the fluid within the tip; a yellow curve could represent the temperature of the fluid within the cooling supply; and an orange curve might represent the tissue temperature as measured by a satellite electrode nearby the heating process or by other indifferent or reference electrodes nearby. The window 613 might display, for example, a graph 634 of the power output of generator 607 as a function of time, and a sub-window could indicate a digital or analog representation of the power P. In window 614, the curve 640 might represent the impedance of the heating electrode 603 or the tissue around said electrode as a function of the heating process. Impedance changes during the lesion process can be of significance. It is believed the impedance will drop as the tissue is heated as referenced by the paper of E. R. Cosman, et al. entitled, "Radiofrequency Lesion Generation and its Effect on Tissue Impedance," *Applied Neurophysiology*, 51:230–242, 1988. As the impedance drops as the RF power heating begins, as illustrated within the window 614 of FIG. 6, there may be small intrangent spikes in impedance, as shown on the curve 640, which would presage or indicate the onset of focal or massive boiling, gas formation, charring, and boiling of the tissue near to or surrounding the electrode or electrode tip. Such spikes or high frequency variations of the impedance can be used to control, monitor, and safeguard the process of the thermosurgery itself. The control system could, for example, be arranged to detect high frequency variations, spikes, discontinuities, or thresholds associated with the impedance, either at high levels or low levels and be used to shut off the lesion process if certain thresholds are exceeded or if certain spikes with narrow time characteristics are detected. There could be electronics to monitor the impedance, or, as a corollary, the power, voltage, current, and temperature (so as to automatically shut down the system, back off the power, modify the cooling supply, or otherwise vary and control the heating parameters for the safety and process of the procedure). Also shown in FIG. 6 is element 610, which may relate to display, chart output, or other recording medium of the various lesioning parameters or ablation parameters such as the temperature of the tip, the temperature of the lesion away from the tip, the current associated with the ablation process, the power of the ablation process, the voltage output at the electrode tip of the radiofrequency generator, the tip geometry of the electrode tip, the cooling flow, the amount of total energy deposited in the tissue, the time course of the ablation, any visualization of the procedure such as a camera readout or display of the electrode position in the patient's body, readout of an ultrasonic scan of the patient's body indicating the electrode position and any aspects of the lesion volume as it proceeds such as cavitation volume, perfusion volume, etc.

As a simple and explicit example of using a two-parameter control system such as 609 in conjugation with computer 611 and input data 620 and prediction or calculation 622 or ultrasonic data 621, one may have a look-up table or function which defines the ablation volume, viz., length and width dimensions, as a function of the tip geometry and tip temperature. The tip temperature $T_0$ could be clamped at a fixed value by cooling fluid or if uncooled, the value $T_0$ is measured by thermosensors. Using tables such as described in the paper of Cosman, et al. entitled "Theoretical Aspects of Radiofrequency Lesions in the Dorsal Root Entry Zone," *Neurosurgery* 15:945–950, 1984, one could predict the width or minor diameter of the prolate ellipsoid of revolution which represents the ablation isotherm and corresponding to say a given power output level from the lesion generator at a given tip temperature near the electrode. This could either be derived empirically from experimental data or could be calculated from the equilibrium equation:

$$kv^2T + \frac{1}{\sigma}j^2 - \frac{dQ_c}{dt} = 0$$

where k is the tissue thermal conductivity, $\sigma$ is the tissue electrical conductivity, T is the temperature in the tissue, and $dQ_c/dt$ is the rate of heat loss due to blood circulation (taken from Cosman, et al., reference immediately above). Therefore, the surface of revolution corresponding to the ablation temperature of approximately 50° C. could be determined as a functional equation, $$S(T_0, R_0, L_0, P_0, x, y, z) = 0$$

This might be the equation of a surface specifying the x, y, z coordinates relative to the tip of the electrode as a function of the tip radius parameter $R_0$, tip length $L_0$, the tip temperature $T_0$, and the power P of the RF lesion generator. This surface S could be displayed in the coordinate system of the electrode or in the 3D coordinate system of the CT or MR data or in a stereotactic coordinate system space referenced to a localizer structure, or localizer marker(s), or external apparatus (arc, frame, etc.) near the patient. The surface could be displayed on the computer as a red prolate spheroid around the tip. Its relation to the defined lesion volume could be obvious by graphic rendering such as done for radiosurgery in the XKnife product of Radionics, Inc. of Burlington, Mass.

Figure 7:
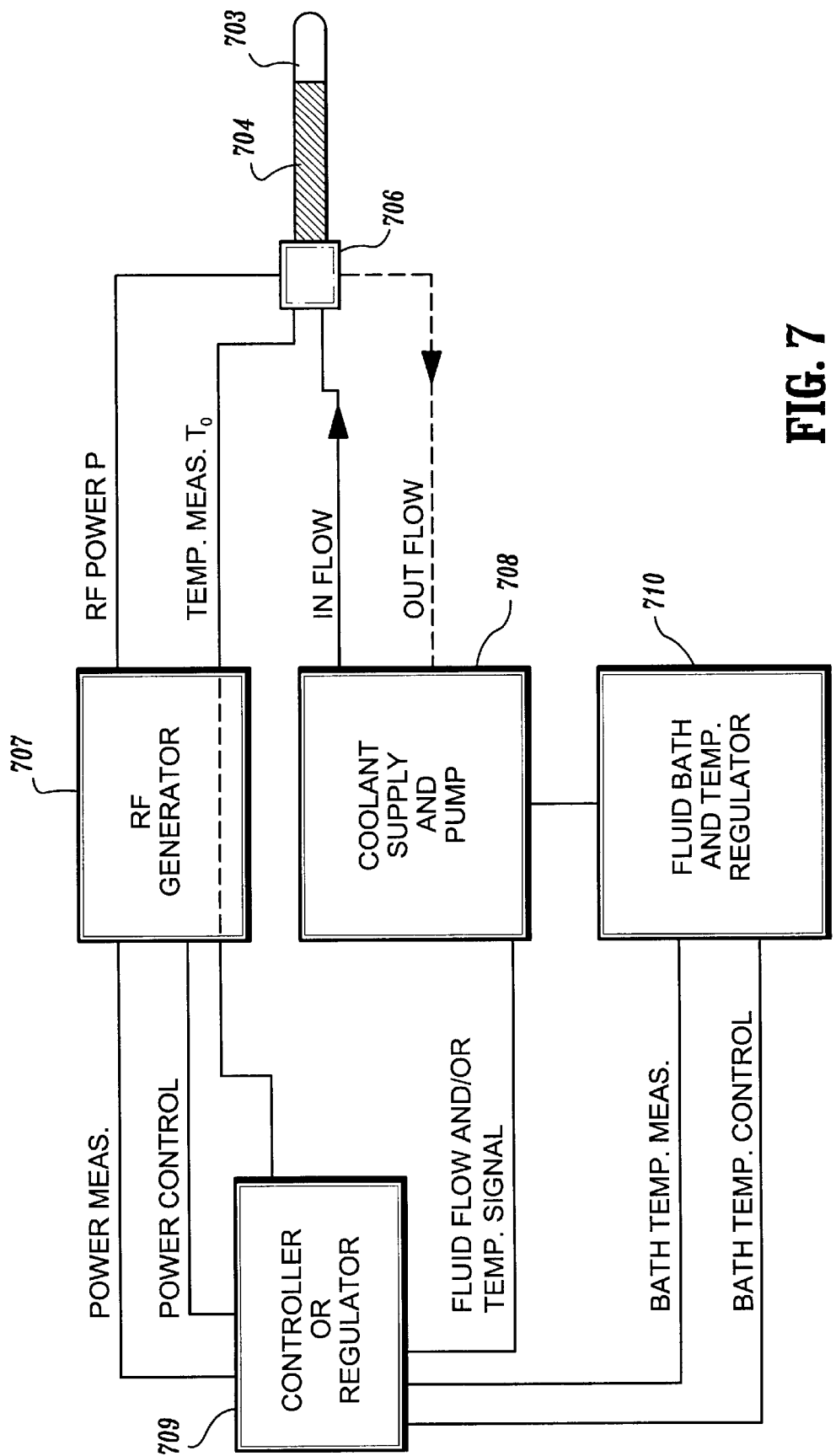
FIG. 7 shows a schematic diagram of a control system for RF heating ablation with a cooled tip electrode showing possible interconnections of the RF generator, coolant system, fluid bath source, and control system to display, monitor, and feed back critical parameters of temperature, power, fluid flow, etc.

Referring to FIG. 7, again an insulated electrode shaft 704 with exposed tip 703 is present and can be inserted into the patient's body so that the tip 703 achieves a target volume to be ablated. Hub 706 has the connection means as described above with respect to FIG. 6, represented in element 606 there. A high frequency generator such as a radiofrequency generator 707 is present and supplying RF power to the electrode, as shown by the RF power P line. At the same time, the electrode, with its temperature sensor, feeds back to the RF generator or controller circuit 709 a temperature reading $T_0$ or multiple temperature readings of a similar nature of the tissue coolant fluid or tip arrangement. According to the temperature reading, a modulation of the RF output power P could be defined by the controller 709 by its modulating the RF voltage, current, and/or power level, accordingly, to stabilize the ablation volume or process. If temperature rises to boiling, as indicated by the temperature measurement $T_0$, the power could be either shut off or severely cut back by the generator 707 or the controller 709. Thus a feedback loop between power and temperature or any other set of parameters associated with the lesion process as described above can be implemented to make the process safer or to monitor the process altogether. Also shown in FIG. 7 are the connections of a power measurement from generator 707 to the controller 709 and a feedback power control signal back to the generator 707 from the controller 709. The entire process of the heating could be preplanned by the operator hours or days before based on the imaging and preplanned calculations of ablation volume with the tip geometry and ablation parameters described with respect to FIG. 6 and in the parent application. Thus, the controller 709 could basically mediate the entire process of supply of RF power P from the generator 707. Similarly, the element 708 represents the coolant fluid supply and pump system with potential thermo-monitoring, pressure monitoring, flow monitoring, etc. Input flow from 708 to the electrode 704 and output flow are indicated by the arrows connecting 706 and 708. Such in and out flow can be monitored by appropriate pressure or flow monitoring elements or detection devices. These are well known in the fluid control industry. According to the controller 709 and the course of the process as is monitored by the controller 709, a signal of fluid flow and/or temperature of the coolant can be fed back between the controller 709 and coolant supply 708 so as to mediate the input and output flow. In conjugation, the combined mediation of flow, power, temperature, or other lesioning parameters could be integrated in the controller or regulator 709, and the entire system of generator 707, coolant supply 708, and controller 709 could be one large feedback control network and system. Furthermore, element 710 could represent the reservoir of coolant fluid with a possible temperature regulation of the bath. Bath temperatures and control signals are fed back and forth to the controller system 709, and these parameters also could be integrated in the overall control of the ablation process. Indwelling controller, electronics, microprocessors, or software could exist to govern the entire process or allow preplan parameters by the operator based on his selection of a tip geometry and overall ablation volume as selected according to a tumor or pathological volume to be destroyed. Many variants or interconnections of the block diagram shown in FIG. 7 or additions of said diagram could be devised by those skilled in the art of fluid control power and regulation systems.

Figure 8:
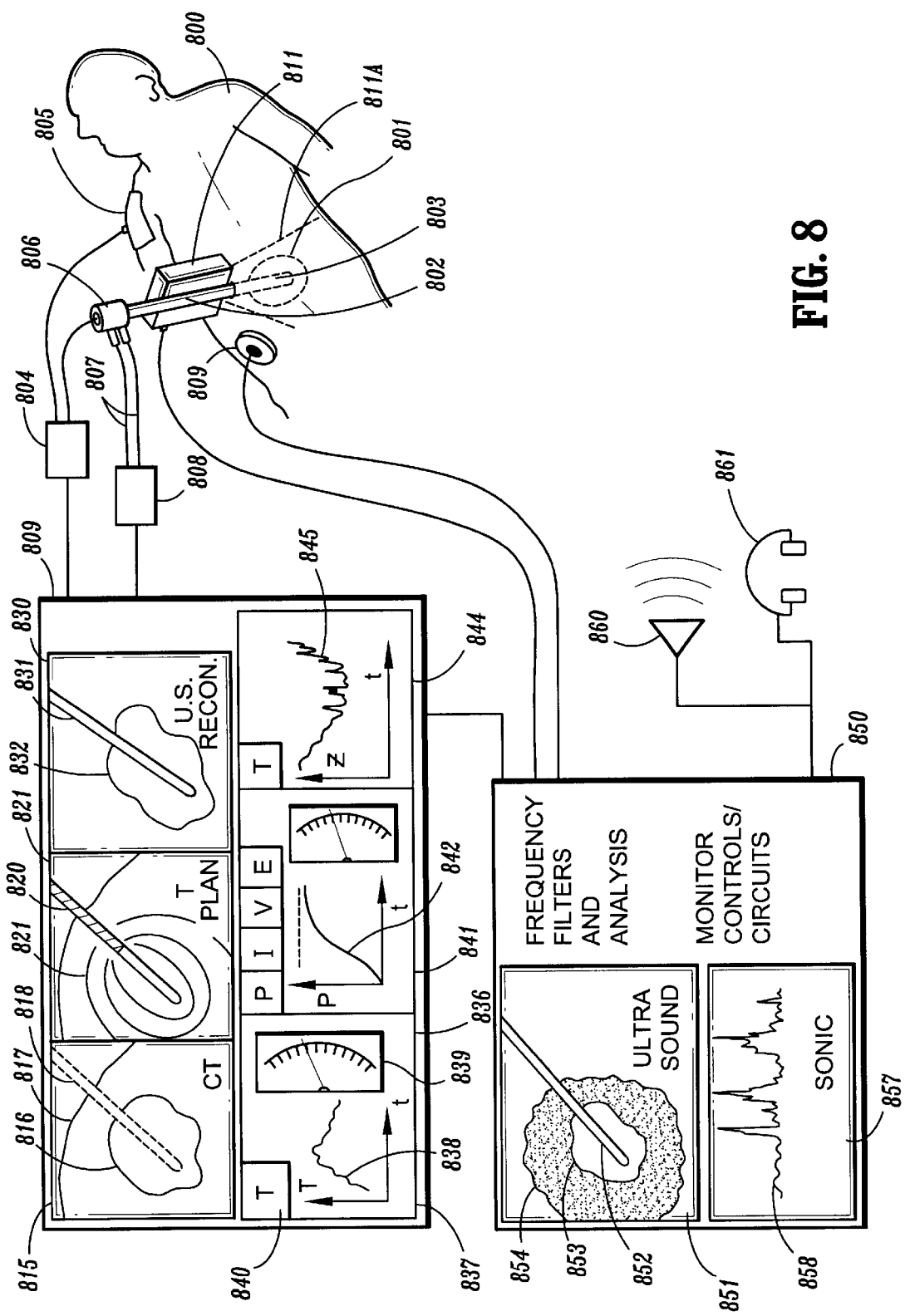
FIG. 8 shows a schematic diagram which depicts a thermosurgical procedure with a probe, cooperatively coupled to an ultrasonic, real-time scanner plus a stethoscope monitor, an interconnection of the RF systems with a computer graphic workstation to monitor imaging, thermal ablation parameters and on-line ultrasonic and sonic imaging and detection. A cooling system is also shown connected to the computer.

Turning to FIG. 8, there is shown an implementation of the present invention which involves, among other aspects, an interoperative ultrasonic and/or sonic monitoring, or other real-time monitoring such as image scanning to control, quality check, and monitor the course of the thermosurgery. The patient's body is represented schematically by element 800, and there is a target volume represented by the dashed line 801. A thermosurgery probe 802 is inserted into the patient's body such that the tip of the probe 803 is placed within the target volume 801. Attached to or in conjugation with or cooperatively coupled with the probe (or probes) 802 is an ultrasonic scanner 811 which, when placed against the surface of the patient's skin or an organ within the patient's body, can be seen to visualize by ultrasonic image scanning a slice or a volume of the patient's body, including the probe and the target volume 801 or the environment around these elements. The probe 802 has cooling lines 807 which connect to fluid cooling element 808 that in turn connects to a control of computer graphic or planning workstation 809. The radiofrequency, laser, high frequency, or other power-generating element is represented by 804; and in the case of a high frequency generator, a return element to a reference electrode 805 attached to the patients body around the shoulder region is shown in FIG. 8. This reference electrode might be a gel pad, large area, conductive pad or other type of standard reference electrode that is used in electrosurgery. This type of circuit for return current for a high frequency generator has been discussed by Cosman, et al. in "Theoretical Aspects of Radiofrequency Lesions in the Dorsal Root Entry Zone," *Neurosurg* 15:945–950, 1984. The ultrasonic scanning head 811 is connected to a monitoring or control circuit 850 which can be used to visualize, analyze, filter, and monitor the image scan data or Doppler shift data or blood flow data or other type of data which is received from the detector 811. This system 850 may also involve power source and processing for the ultrasonic-scanner. Such ultrasonic scanners are well known in the medical industry and are represented by, for instance, the product of the Aloka or Siemens medical corporations. Within the control monitoring, preplanning, and feedback unit represented schematically by the box 809 are various visualization windows which are used here as illustrations. For example, in window 815 there may be represented in 2D or 3D slice or volume representations image scan data taken from an image scanner such as CT, MR, PET, or ultrasound prior to, during, or after the thermal ablation. In this instance, the patient's skin 817 is defined, a target volume 816 is shown, and in the dashed line is a preplanned path for a thermal ablation high frequency electrode. By means of such visualization, the probe path 818 can be manipulated within the image or image stack of CT or MR slices, and an optimal path for placement can be achieved. This path could be achieved by criterion from the surgeon such as bringing the probe path along a principal axis of a tumor 816 or from a direction which avoids some critical structures such as arteries, lung, optic nerve, neural structures, etc. Thus, based on the historical image data, the surgeon can do a preplanned study and decide on the optimal positioning of his electrode which he ultimately will place within the patient's body. In addition, the electrode could be placed stereotactically and guided by either a stereotactic arc or a frameless stereotactic navigator or digitizer, these devices being represented by the product such as the CRW Stereotactic Frame and the OTS Optical Tracking System and OAS Operating Arm System by Radionics, Inc. in Burlington, Mass. In the second visualization window 821, a thermal plan can be devised based on, for example, RF generator parameters and cooling parameters. Here a path or hypothetical or preplanned probe position and dimensions 820 are shown on the window approaching the tumor volume. By means of a calculation, algorithm, look-up table, or clinical experiential data, for given values of the cooled thermosurgical tip and power or current or voltage output of the RF generator, isothermal surfaces can be predicted within the patient's body around the high frequency electrode exposed tip. These might be represented graphically by the lines 821. The lines can have varying colors depending on the temperature. For example, red lines being hottest and blue lines being coolest as one goes asymptotically to body temperature at larger distances. They can be a quantitative temperature scale to indicate the color coding, or digital thermal representations on each of the thermal isotherm surfaces can be rendered. Threshold temperatures set by the operator, for example at 50° or 60°, could be shown by red and blue surfaces or volumes. All such graphic manipulations could be done as a preplan for thermal surgery prior to insertion of the probe. In the window 830 is shown a real-time representation of the probe 831 as it is inserted into the patient's body. The margin 832 may be a reconstruction, either theoretical or actual, of what one would expect to see from either the tumor volume or the result of the RF heat ablation itself. For example, if the window represents an ultrasonic reconstruction, this could be a theoretically generated graphic representation within a preplanned ultrasonic slice direction and probe direction to show what the ecogenic or ultrasonic image would look like when certain cooled tip RF generator parameters are invoked or used. This window may alternatively represent real-time image data from the CT or MR or other type of scanning means, if the patient is within such a scanner during the RF heating process. It could represent the changes or modifications or digitally subtracted differential changes of the tissue volume as a result, directly or indirectly, of the ablation isotherms. Thus one may visualize directly the effect of heating on the patient's tissue, and this may be displayed in such a window. There may be a superposition of a preplanned or prescanned tumor volume, as compared to the actual volume of the tumor at the time of surgery or the ablation volume as one detects it during surgery. Also shown in the window 836 is a graphic display of the temperature at one or more of the thermal sensing positions associated with the heating probe and its tip 803. A graphic rendering of the temperature graph 838 may give an exquisite temporal representation of variations or absolute values of the temperature on a graph plotting temperature as a function of time (temperature axis T and time axis t). Also shown is a representation of an analog meter 839 with a meter dial and scale as in a standard electronic meter which can show the time course of the temperature increase at the electrode tip of the surrounding tissue. Such a representation along with the graph may be important to visualize the time rate of change or temporal derivatives as the procedure goes forward in time, giving the surgeon an instantaneous sense of the correctness or possible problem with the heating such as transient boiling or runaway to higher temperatures. Further shown is a digital display 840 of the temperature which gives an instantaneous, easy to understand view of the temperature at one or more points in the tissue or electrode tip. In the panel 841 may be shown other important parameters associated with the RF generator or cooling fluid agent. Here is shown a graph 840 of, for example, the power output of the generator to the electrode on a graph with vertical axis P for RF power and a horizontal axis t for time. Thresholds may be set for either P or t in either of these graphs, and these set points may trigger control elements to shut the generator off, increase power, or other functionality. Also shown in the upper portion of this window 841 may be digital displays of many parameters such as power, current, voltage, energy, time associated with the thermal ablative process. In the window 844 is a representation of the impedance of the entire active electrode 803 and inactive electrode 805, together with the intervening body tissue. This impedance Z is an overall or measure of the uniformity of heating, the change of the tissue characteristic in the ablation process, the onset of boiling, incipient or local boiling, gas formation, charring, etc. Any disconnection of the cable or electrode would also be represented as a dramatic change in the. impedance parameter Z. As shown in this graph, as the horizontal axis is t, and the vertical axis is Z, one sees as the power is increased and the temperature increases, the impedance decreases indicating the decrease in resistance or the increase in mobility of the ionic medium of the body tissue. This is understood from the paper of Cosman, et al., "Theoretical Aspects of Radiofrequency Lesions in the Dorsal Root Entry Zone," *Neurosurg* 15:945–950, 1984. As the impedance decreases, transient or high frequency variations of the impedance may occur, as shown in the graph 845, and indeed there may be a precipitous rise of the impedance indicating the onset of gross boiling or tissue charring or tissue characteristic changes. Such spiking or high frequency impedance changes could be an indication of focal boiling or erratic behavior of the process which could warn the operator to monitor the situation closely or abort the process.

Also shown in FIG. 8 is real-time monitoring of the lesion process or target localization. This is represented, for example, by the ultransonic display in window 851 of the ultrasonic control and power system 850. This system may have special frequency filtering and spectral analysis and other controls and data display circuitry so as to visualize an ultrasonic "fan" or slice in the body as the RF electrode is being placed and the RF thermal surgery is being done. Since ultrasonic detectors are well known in prenatal observation of fetuses within the woman for a diagnosis and visualization real time of structures within the body. Shown in panel 851 is the probe 852 within a tumor 853, both of which may be visualized in ultrasound. The perimeter 854 may be a characteristic zone of thermal destruction which, for example, may have different ecogenic properties after heating and which also may have different blood perfusion characteristics as the heat process goes forward. For example, heating of tissue gives rise to closure of blood vessels which means that the perfusion or blood flow on a microscopic and semi-microscopic basis shuts down. If the ultrasonic detectors are very sensitive to perfusion and flow, this can be a characteristic change as seen on the ultrasound which is analogous to and representative of the ablation volume. Such real-time monitoring of the process could be extremely important in controlling and limiting the degree of heating and the borders of the thermosurgery. Such a panel could also represent real time, CT, or MRI images, which are done in a similar way and where characteristic changes can be seen. This will be explained below with respect to CT, for instance, where use with contrast medium during the procedure can exquisitely show the border of perfusion to non-perfusion and thus delineate the region of radiofrequency heating exactly. This is real-time imaging feedback at the thermosurgery process which is claimed here and in the parent application as an important adjunct to this technique and invention. Similarly in MRI, breakdown of the blood-brain barrier and shutoff of perfusion gives rise to characteristic changes that can be visualized during surgery, and these, too, can be used as mode of monitoring. Also shown in panel 857 is feedback from a stethoscope 859 that can be placed on the surface of the body or within the wound during a thermosurgery procedure. The graph 858 shows the amplitude or frequency analysis of a sonic signal from such a stethoscope. The stethoscope illustrated by element 859 can be a standard stethoscope, an electronic stethoscope, or a multiplicity of sonic detectors of any kind that can be placed on the body in the region or near the region where the thermosurgery electrode 803 is being placed. The element 850 can have radio amplifiers and filters to detect the signal from the stethoscope or microphone 859 so as to pick up audio or audible signals or noises from the depth of the body. Such stethoscopes are used regularly by physicians in listening to the chest cavity, bowel, and other areas of the body to detect very sensitively physiologic changes and activity. In the process of making a thermal ablation as described in the parent and this present continuation-in-part application, the heating process can induce changes with respect to blood flow or perfusion of blood within the ablation volume. This can give rise to detectable audio changes. Frequency analysis of the audio changes may also be possible within the unit 850, and thus the frequency spectrum or differentiation of frequency response from such audio signals can be analyzed to pick up high frequency, low frequency, or broad band spectra. The graph 858 might indicate, as a function of time on the horizontal axis, the audio signal from such a microphone. At first, normal base line signals are heard. Variations from that, as the heat process continues, may indicate the onset of decreased perfusion within the tumor volume. Spiking or irregular, erratic high frequency signals could indicate the onset of cavitation or micro bubbles at the region of highest heat. As this continues, the amplitude may increase and frequency as well, signaling to the operator a potential avalanche towards microscopic boiling. Also indicated in FIG. 8 is a speaker 860 or earphones 861 which can aid the operator in sensitively detecting any of these audio signals from the microphone 859. The microphone could also be embedded within the probe 803 for very sensitive local recording of variations of audio signals from the lesion process. This has an even more sensitive pickup of local changes in blood circulation, especially with respect to arteries and perfusion within a target volume and with respect to microscopic cavitation due to gas formation and bubbles as the heating process goes on.

Thus, included within the scope of the present invention is the use of a computer graphic workstation, as illustrated in the example of FIG. 8 in which preplanning with imaging is involved, planning of isotherms and prediction of such isotherms in the thermosurgery is done with respect to or not in respect to the 3D position of the electrode, comparison to historic, contemporaneous or post-image reconstructions of the anatomy, both differentially, before and after, and/or absolutely, and to detect the appropriate position and angulation of the electrode with respect to the target volume as well as any effects from they thermosurgery itself. Direct detection of changes in the physiology as a result of the heating to gauge the extent of the ablation volume can be done by ultrasound, CT, MRI, PET, and other imaging modalities, and can be displayed on the graphic means of the thermosurgery computer system or, indeed, on the graphics display of the ultrasound or CT, MR, or other scanning machine as supplied by standard manufacturers. Each of these scanning devices has a graphics display on a CRT, liquid crystal, or other means which can display the results of the tomographic or volumetric scanning. These can be used in conjugation with the thermosurgery to evaluate the effect of the thermosurgery itself. Use of ultrasound and standard sonic detection and scanning may be used in conjugation with the thermosurgery to evaluate the effect of the lesion or ablation process. Those skilled in the art can make variations of these concepts and make their own examples of systems and displays in conjugation with thermosurgery, and these are intended to be within the claim and scope of the present continuation-in-part and parent application.

It is noteworthy that the use of the ultrasonic detector 811, which accumulates ultrasonic slices subtended between the dashed lines 811A and 811B, means that one can "watch" the ablation process as it occurs. Also, because the microbubbles formed prior to macroscopic boiling give rise to cavitation and are ecogenic, this gives a real-time view via the ultrasonic detection of the volume such as 854 to monitor the ongoing thermosurgery process, real-time.

It is noteworthy that in connection with FIGS. 6, 7, and 8 the invention includes the measuring and/or the control or use of one, two, or more parameters such as the tip temperature of the clamped thermosurgery tip, and the power of the high frequency generator. These two parameters may act independently and can be selected by the operator so as to produce the appropriate kill isotherm or ablation volume. Other parameters may be invoked, all of which can be controlled in a multi-parameter space according to algorithms or experiential paradigms and models. For example, in FIG. 6 the control system may manipulate the temperature $T_0$ of the tip 603, the power P from the RF generator 607, the current I from the RF generator 607, the impedance Z of the electrode tip 603 in series with the surrounding tissue, and the indifferent electrode, which is not shown in the circuit of FIG. 6 but is implicitly there as described above and in the parent application. Thus, beyond simple geometric factors such as the size and shape or configuration of the electrode itself, the control system such as 609 or 709 or the computer graphic workstation with its control circuitry and for software 809 may manipulate these parameters or control them as independent or semi-independent parameters to produce the appropriate lesion size, the rate of change of production of that lesion size, the growth of the ablation isotherms, the asymptotic size add shape of the ablation isotherms, etc.

We are also claiming and including the simpler case of controlling only one parameter such as RF current or RF power, and simply forcing enough coolant fluid into the electrode to assure that proper tip cooling is being done. For example, using nearly room temperature saline or water or ice water may serve this purpose. This is a simpler approach, but may be effective in some cases where criticality is less important.

Figure 9:
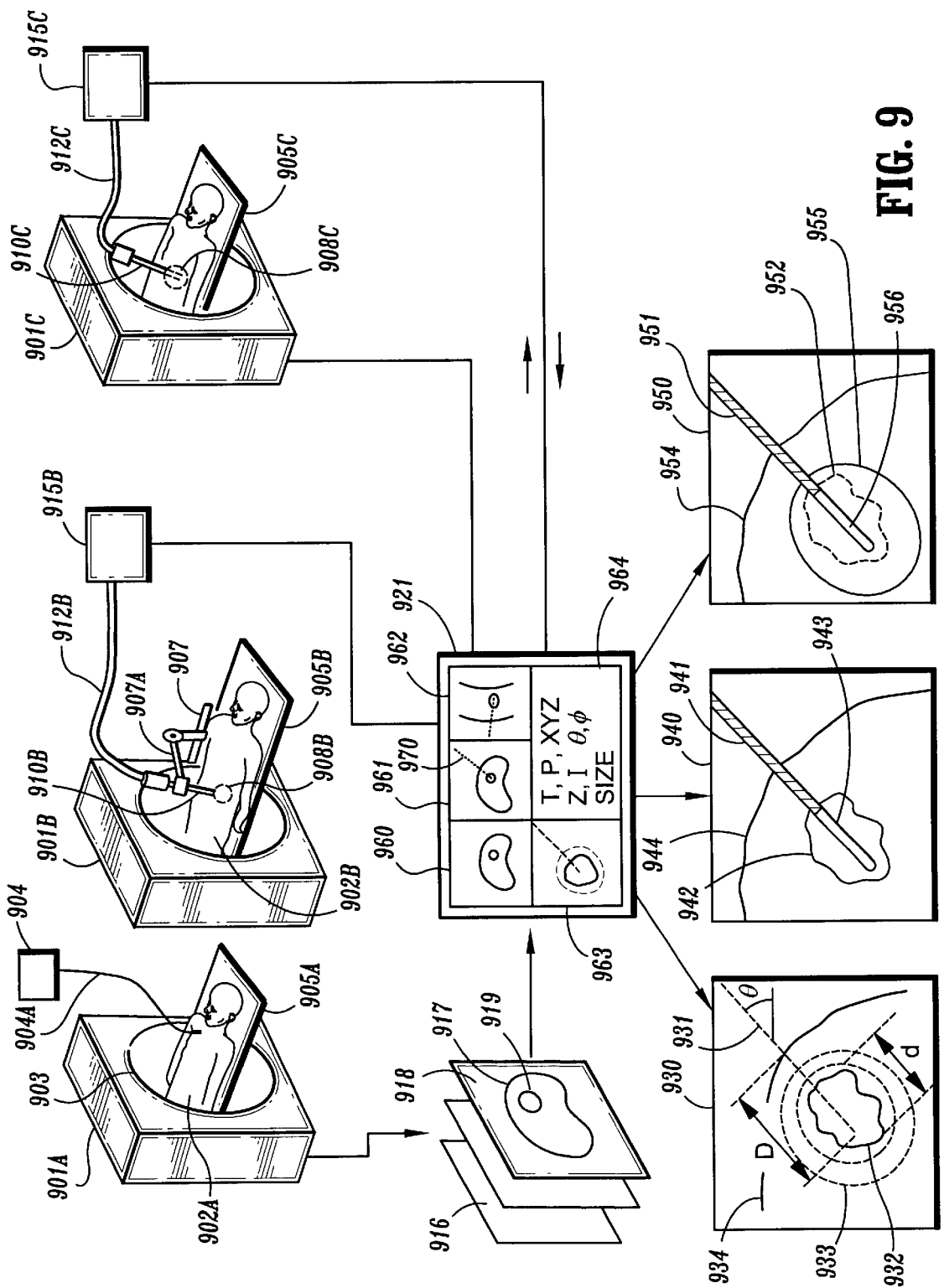
FIG. 9 depicts an embodiment of a method and procedure using the thermosurgical equipment of the present invention, including the sequence from pre-ablation scanning, stereotactic electrode placement and planning, ablation control parameters, and possible post-ablation confirmational scanning which may include contrast enhancement or special image scanning or image data processing for detection of the thermal destruction region.

FIG. 9 shows schematically another example of apparatus and method which can be used to illustrate the presents continuation-in-part invention and the parent patent application. The example will be to use tomographic imaging of any type in conjugation with the cooled tip or non-cooled tip, high frequency electrode thermal heating method (or thermosurgery), or in conjunction with other heat deposition methods such as laser, microwave, radiofrequency, etc. to menitor, preplan, and detect, real time or after the thermosurgery, the effect of the thermosurgery on the target volume and the possible further use of that imaging information to alter the course of the thermosurgery or augment it. In the upper left portion of FIG. 9 is shown a schematic diagram of a tomographic image scanner 901A. This may be an X-ray computer tomographic (CT) scanner, an MRI scanner, a PET scanner, an MEG (magnetic encephalography) scanner, a SPECT scanner, or any other tomographic scanner present today or devised in the future. Typically, these devices have an aperture 903 to which the patient's body 902A can be inserted during the scan process. The patient is lying on a couch or table 905A which can be inserted more or less into the aperture 903 so as to gain image data at different portions of the patient's body 902A. Schematically, a set of image scan data represented as slices or tomographic cuts through the body will be acquired and stored in a computer system for access, rendering, graphic representation, and manipulation. Such slices are indicated schematically by the slice 916 and 918. In these slices would be tomographic image of the patient's body such as 917, and inside the body might be a target volume 919 such as a cancerous tumor, arteriovenous malformation, or other structure. Also included in the tomographic scan are representations of normal anatomy and critical structures which wish to be avoided during the passage of a thermal probe into the body or in the thermosurgery ablation. The image scan data from the image scanner can be transferred in the course of this invention to a computer graphic workstation 921, which may have graphic representations on a display means such as a CRT, liquid crystal screen, or other graphic representation such as printouts, chart recordings, etc. In one of the windows 960 of the display of the computer graphic workstation 921 is shown the slice 918, for example, so that this can be reviewed by the clinicians at the time of surgery. Catalogs of such image scan data can be taken from multi-image sources such as CT, MRI, etc., put on the same computer graphic workstation, the images can be fused together and overlaid (see the article by E. Alexander, et al. *J. Neurosurg.* 83:271–276, 1995.) and manipulated in 3D for graphic renderings of a variety of types. (Such graphic renderings and manipulations are illustrated by the XKnife Radiation Treatment Planning System of Radionics Software Applications, Inc. in Burlington, Mass.). Also shown in the scanning phase is element 904, which may be a source of contrast medium that can be infused into the patient's body, as indicated by the infusion line into his arm. This is commonly done in CT scanning to enhance images, and such enhancement can also be present during or prior to scanning for other methods such as PET scathing, MRI scanning, and other tomographic image methodologies. It is also used for angiographic and X-ray scanning, if that is the means of imaging taking place which is also subsumed in this discussion. In the top middle portion of FIG. 9 is a schematic rendering of the patient undergoing thermosurgery. Here the couch 905B has been pulled out so that access can be made to a portion of the anatomy which is seen in the tomographic slice, for example 918, when a patient was further inserted into the gantry, as in the position 905A of the couch. A dotted volume 908B would represent a target volume within the patient's body, seen in the image data, that must be approached and achieved by the thermosurgery probe 910B. The probe may be inserted stereotactically into the body either through the skin (percutaneously) or intraoperatively into the target structure 908B such that the exposed tip, if it is a radiofrequency electrode, is within the tumor or target volume. In this instance, a holder and/or stereotactic guidance device 907A is secured to the probe 910B so as to direct it and/or stabilize it in a given direction upon its path into the body. A clamp device or attachment 907 to the stereotactic holder 907A may secure it stably to the couch 905B. As will be discussed below and in the art of stereotactic instrumentation, such a device can be used to direct a probe into the body based on image scan data with or without reference indicia derived from that image scan data when the patient has been scanned using a graphic reference means or reference marks on or in the body, or natural landmarks referenced by a frameless stereotactic navigator. Reference, too, can be made to the patent of Russell Brown, U.S. Pat. No. 4,608,977, Sep. 2, 1986, for further details that exemplify this stereotactic usage with a reference localizer structure or to B. L. Guthrie and E. R. Cosman, U.S. Pat. No. 5,230,623, Jul. 27, 1993 in the case of a digitized navigator. Claimed within this invention is the use of the thermal ablation probe together with a stereotactic instrument, and together with the use of a computer and computer graphic guidance to preplan and implement the positioning of such a probe within the patient's body. Applicator 907A and its base 907 may have translation scales in Cartesian, or polar, other arc coordinates so as to angulate and position the probe in a desired trajectory or path to achieve a target position or volume such as 908B. Also shown is element 915B, which may be a complex of radiofrequency generator, cooling fluid control system, feedback control system, etc., as has been exemplified by the embodiments above and in the parent application. There is a connection shown between the element 915B and a computer graphic workstation 921 which may include a control system which may be used to mediate the power, cooling, flow, lesion parameters, and other factors associated with the ablation process as has been described above and in the parent application.

Referring to the upper right portion of FIG. 9, this may show the situation after the probe has been placed into the tumor volume and confirmed by scanning where the patient is returned back into the scanning volume and more imaging is done to confirm its position and/or to monitor the course of the heat ablation. Again, the RF generator and fluid control system, plus other controls described above, are schematically illustrated as element 915C with the connection to the electrode 912C which may be both an electrical and fluid-carrying means. The couch 905C is shown drawn back into the gantry of the scanner 901C so as to visualized by imaging the position of the electrode within the tumor volume. In this figure, the tumor volume may be represented by the dashed volume 908C, and the electrode being 910C. At this phase in the thermosurgery, information from 915C may be transferred back and forth from a controller and data collection, computer, or computer graphic workstation such as 921.

Turning to the images and representations that are possible in a computer graphic workstation/controller such as 921, the image 961 may represent a preplanned, predicted, or calculated path of a probe which might be represented by the dashed line 970 shown in relation to the patient's anatomy on a display of a tomographic slice such as 918 with a representation of the target volume which, for example, may be a contoured region or a segmented region within the image. Window 962 may show a similar picture of the patient's body, but from a sagittal or coronal view or some other reconstructed plane which may, for example, include the line of the thermosurgery probe. In image 963, there may be an image of the probe path, preplanned or actually imaged as in the upper right of FIG. 9 during actual re-scanning of the patient, the tumor volume shown as the solid closed contour may be shown, and the dashed line may represent isotherms, either preplanned, calculated, or actually detected from contemporaneous or post-imaging following thermosurgery. The window 964 may show a variety of parameters related to the thermosurgery, including the temperature T of tissue, the tip, or the coolant, or multiple temperatures at different positions on the tip or nearby tissue, the power output P of the high frequency generator, the impedance Z of the tissue and electrode or electrodes, the current I of the output of the high frequency generator, the size of the electrode tip, or other parameters such as time, voltage, frequency, etc. In addition, it may display various coordinate or stereotactic coordinate positions, either pre-plan ned or actual, associated with the approach of the electrode to the target or the settings of a stereotactic frame, or the orientation of the probe as actually measured by a contemporaneous or post-scan, as shown in the upper figures. The coordinates X, Y, Z, for example, may represent Cartesian coordinates of the average position of the thermosurgical probe, theta and phi represent the polar coordinates corresponding to the angulation of the probe relative to a body-fixed or scanner-fixed coordinate system. The surgeon, therefore, by looking at the display of computer 921 may have an instant visual appreciation both of the image scan data, the preplanned calculation of approach, and the actual approach with real-time update from imaging, including the size of the heat ablation volume as seen during or just after heating. Thus, as part of the parent application and this continuation-in-part, there is claimed the use of such a computer graphic workstation to monitor and control the entire thermosurgery process.

The lower portion of FIG. 9 gives more detailed illustrations of some of the possible windows or panels in the computer graphic workstation 921 that relates to the preplan and the course of the thermosurgery. The claim 930 may appear on the computer graphic workstation and may be a preplan or a contemporaneous view of the procedure. For example, in a tomographic slice or a reconstructed tomographic slice, the skin 934 of the patient's body is shown and could be automatically segmented. The tumor or target volume 932 may be automatically segmented or the surgeon may outline it himself. A path 931 may have been chosen by the surgeon or may be the actual path of the probe when it is inserted. An angle such as theta may schematically illustrate the polar coordinates or other angular coordinates represented by a stereotactic approach relative to the coordinate system, for example, of the CT scan slices such as 918 or a stereotactic coordinate system associated with a stereotactic frame such as 907A and 907. The positioning of the probe path 931 may be preplanned and optimized by a variety of methods. The surgeon may do it simply visually by inserting and manipulating the line position in the computer graphic workstation space. Alternatively, an automatic plan or "auto plan" may be invoked in which optimization or isotherms may be calculated by the computer by means of an algorithm, look-up table, or other methodology, and by varying the position of a preplan probe path 931, an optimization of the probe position and thermal heating of the volume 932 may be achieved by a computer theoretic method, which for example may be to get desired or best coverage of the tumor volume with the ablation or "kill" volume, but minimizing the involvement of the heat ablation volume on normal surrounding tissue, especially critical structure which may have been outlined or segmented by the clinician beforehand. An example of such auto plan planning in another context of X-ray radiosurgery can be referenced to the product of XKnife by Radionics Software Applications, Inc. in Burlington, Mass. This illustrates how such automatic planning can be implemented, and it could be invoked for the neurosurgery technique described here, either for cool-tip or non-cool tip electrodes. The surgeon, for example, may invoke not only the geometric and physical parameters associated with thermosurgery, but also invoke an atlas of thermo-sensitivity of surrounding normal tissue so as to optimize, by means of a mathematical algorithm or software, the degree of involvement of the thermosurgery with the normal tissue and the degree of coverage of the thermosurgery isotherms to the target volume. Thus, other parameters may be invoked in optimizing a thermosurgery plan other than simple geometric, electrical, and temperature parameters. Thus this invention is intended to claim automatic planning and preplanning of thermosurgery based on thermal sensitivity, blood flow, biological characteristics, physiologic geometries associated with the anatomy of the patient in selecting an optimal set of isotherms or thermosurgery zones. Geometric parameters such as the dimension of the tumor, illustrated schematically by d in the frame 930, may govern the selection of the exposed tip of a high frequency electrode or the diameter of said electrode. The depth from the patient's external skin to the position of the high frequency electrode in the target volume, illustrated schematically by D, may be a parameter which is used in the stereotactic approach and in determining the depth of penetration once the electrode is placed in the patient's body. Thus the frame 930 illustrates some of the parameters associated with the preplan. Also shown are dotted lines or zones 933 which represent various temperature isotherms which could be predicted or which can be actually seen and measured during the course of thermosurgery. The isotherms, for example, can be calculated knowing the clamped temperature $T_0$ of the high frequency tip together with the power, current, and/or impedance of the tissue and the electrode in the tissue so as to predict mathematically or heuristically, by means of an algorithm or software program, the spread of temperature and the fall-off of temperature as a function of distance and angle away from the tip. Thus, displaying such isotherms 933 could be very helpful to the surgeon in predicting the optimization of his probe position and the degree of high frequency power, the temperature of the tip, the flow of the coolant, etc., so as to optimize coverage of the target volume but to minimize the destruction of normal tissue nearby the ablation volume.

The window 940 may also be shown on a computer graphic display and may represent the next chronological step in the sequence of thermosurgery. Whereas the window 930 described above may relate to a preplan, the window 940 may relate to an actual visualization or placement of the thermoprobe 941 within the target volume 942. This picture, for example, may be an actual imaged picture from CT, MR, ultrasound, PET, or other imaging modalities showing the electrode 941 in place. The hatched region of the electrode 941 may be its insulated shaft, and the tip 943 may be the exposed electrical active tip for emanation of high frequency current into the tissue. The tumor volume 942 is being lanced by the electrode 941 in preparation for thermosurgery. This patient's skin 944 is shown in this reconstructed image from tomographic scanning such as slices 918. At this point, for example, confirmation of an electrode or an electrode's position or probe or probe's position within a target volume can be determined by contemporaneous scanning.

Window 950 of a computer graphic workstation 921 may represent the next chronological phase in thermosurgery. Here the heat ablation is being applied, and a region of actual heating 955 may be visualized on the imaging apparatus as may be implemented by the schematic figure in the upper right of FIG. 9 already described. The dashed line 952 may represent the position in space of the target volume or tumor volume. The patient's skin 954 is also manifest, and of course the electrode shaft 951 with its exposed tip 956 is also seen. It is claimed within this application and the parent application that actual real-time visualization of the lesion volume or representations which are proportional to the heat ablation volume as may be determined or detected during imaging or derived from image data and can be used to control the course of thermosurgery. To give one illustration of this, if during the image scanning or image data collection an infusion of contrast agent, viz. via the unit 904, is delivered to the patient intravenously, then the degree of blood or contrast agent circulation or perfusion of tissue can be visualized. For example, a contrast agent, which in fluid form can be injected into the blood stream is carried to all portions of the body in a time sequence flow. If during thermosurgery the blood supply of small capillaries, arteries, and veins are shut off as they are by the elevated temperature, then the perfusion or inflow of such contrast agents into a tumor volume or into a thermal ablation volume will be severely reduced, if not brought to zero that means that there is a strong differential visibility of the ablation volume as seen in a CT tomographic scan or an X-ray radiographic image because of the effect of shutting down blood perfusion in the thermal ablation volume. This, therefore, gives a very sensitive means of visualizing the thermal ablation volume by infusing an X-ray contrast agent at or about the time of thermosurgery, and then doing an X-ray (CT) tomographic scan or an angiographic scanning of the patient's body to visualize the thermal ablation volume as a region of lack of contrast infusion. This is simply one example of how contemporaneous or post-scanning of the patient's body can directly visualize and monitor the size and extent of the thermal ablation volume. Claimed in this patent application is the use of such contrast agents or other methodologies which may be thought of by those skilled in the art to visualize the effect of thermal heating around the high frequency electrode or probe during thermosurgery. That volume as seen by such scanning may be illustrated by the ring 955 or a darkened region where no contrast is seen as a result of the heat ablation.

For point of other illustration, another means of visualizing directly the effect of thermal ablation and the extent of the isotherm corresponding to or substantially approximating the total ablation of cells can be performed with MRI imaging. It is known that MRI imaging is sensitive to blood flow, and indeed in some cases can measure high velocity and low velocity blood flow, as for example in the flow of large vessels or the perfusion of small vessels, respectively. Thus, it is possible, with certain T1 and T2 weighted images and/or spin echo and echo recovery sequences, to directly visualize the effect of blood flow in the body (reference to *Nuclear Magnetic Resonance Imaging—Basic Principles*, Stuart W. Young, Raven Press, New York, 1984). Therefore, by monitoring with MRI before, during, or after the thermosurgery, differential measurements can be made which are directly indicative of blood flow and therefore the shutting off of blood perfusion during the thermal ablation process. This, therefore, would be a very sensitive imaging method of determining directly the extent of the kill volume or the isotherm of death for ablation cells during thermosurgery. For example, the use of MRI-compatible thermosurgery probes such as 951 would enable artifact-free imaging during MRI, post-thermosurgery, or contemporaneous thermosurgery to determine the extent of the kill volume 955 or other isotherms. Also, the character of the cells themselves or the protein, DNA, cell microstructures, biochemical and chemical bonding environment, hydrogen bonding, etc. will be changed during thermosurgery, and this too may be detectable by the proper T1/T2, spin sequenced, contrast enhanced, spin-echo, or differential image enhanced or other modality of MRI imaging. The advances in MRI and CT images are very rapid at this time in history, and therefore those skilled in the art may think of other sensitive detection means using CT or MRI which will further exquisitely show the extent of the thermal ablation volume. For example, in the case of CT, MRI, PET, SPECT, MEG, angio, or other imaging techniques, the breakdown of blood brain barrier, or the alteration of the character of cells and the DNA, or the interface between ablation kill and normal tissue with respect to differential blood diffusion, or biochemical uptake, or metabolic activity of normal versus dead or dying cells, or the differential between cancerous cells and non-cancerous cells or thermal sensitive effects such as chemical shift, frequency shift, metabolic processes, spin-spin relaxation or other relaxation phenomena, susceptibility changes, all of which can be sensitively affected by heating, or the molecular/atomic effects of heat may be invoked to show other aspects of the isotherms in great quantitative detail or in sufficient qualitative detail for the operator to determine, real time, the extent and effect of thermosurgery. These are all claimed as adjuncts to the thermosurgery method described herein.

We claim the use of image differential and/or image subtraction techniques to show the heat region or the effect during or after heating of the target volume. As an illustration, in the image 963, or 940, or 950 of FIG. 9, what might be shown here is the difference between a CT, MRI, or other scan image before and an image during (or after) heating. The two images or image slices may be in spatial registration and thus subtracted or otherwise added in a linear or non-linear manner to show small differences in the two images as a result of the thermo-ablation. We claim the use of such differential image data in connection with thermo-surgery to more sensitively bring out subtle or small changes which can represent the ablation kill volume or the change in the tissue environment. Here "image fusion" or special or stereotactic merging or co-registration of before-during-or after data sets could be handled in the computer, and displayed in various ways to bring out the thermo effects.

As a further note on the method and embodiment, ultrasound can be invoked, and ultrasonic imaging can be very sensitive to thermal effects. For example, the electrode 951 with its exposed tip 956 may have ecogenic or non-ecogenic materials on the insulation or the exposed tip so as to directly visualize the extent of the exposed tip or the insulative shaft. In this way, the electrode may be "seen" with ultrasound, and the exact position of the exposed tip may be differentiated from the insulative shaft. For example, the shaft 951 which is insulative may be made of a plastic material, whereas the tip 956 may be made of a metal material, and the metal surface of 956 may be made rough or eco-sensitive so that there is a clear visual differentiation between the insulative shaft and the exposed tip by means of ultrasonic imaging. This is claimed within the scope of the present invention. Ultrasonic imaging may be used to directly visualize an isotherm or iso-ablation volume 956 directly with respect to a target volume 952, since the ecogenicity, Doppler effects, change of density, or other characteristics of the cells may be differentiated by advanced ultrasonic, three-dimensional, color-encoded ultrasonic imaging technology. Thus the example of FIG. 9 shows an embodiment and method which is practical today for preplanning, guiding, controlling, and visualizing the exact effect of thermosurgery on a target or tissue volume.

It is claimed within this invention that the monitoring of ablation parameters such as tissue temperature, power, current, impedance, and the display relative to a three-dimensional representation of where the tip resides or is placed with respect to a target volume is a novel and unique aspect of the present invention. The computer graphic workstation and/or control systems mentioned above can make use of this and display real time for the surgeon how these parameters interplay to engulf the tumor. Representations of the lesion volume are possible as a preplan or post-image detection for this purpose.

Figure 10A:
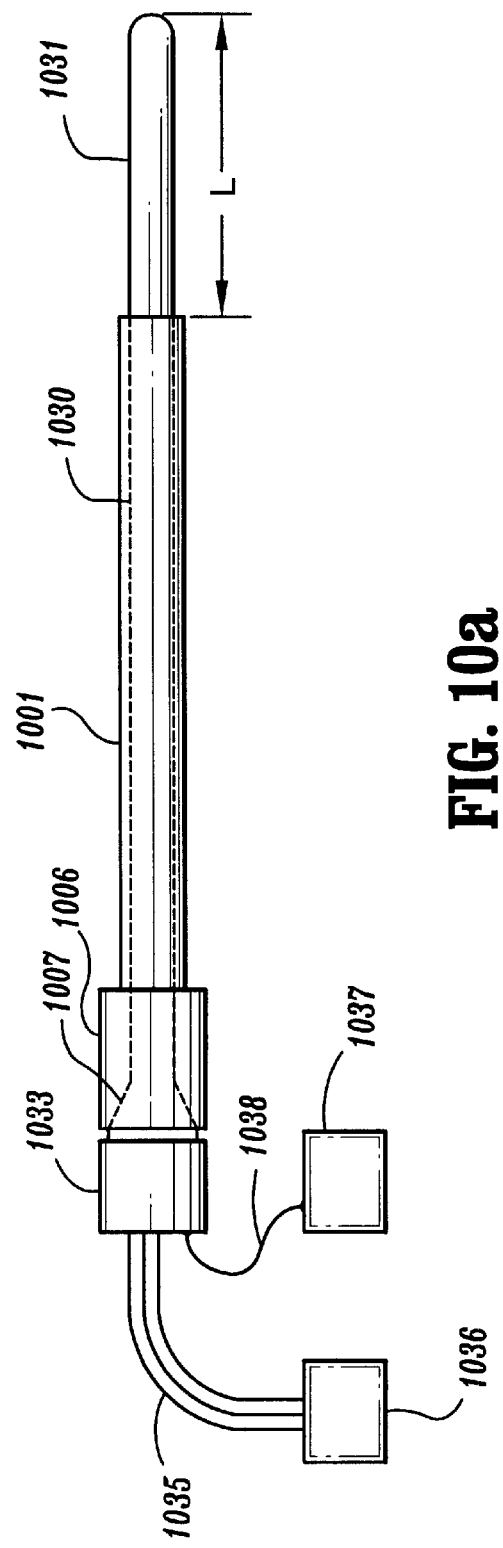
FIGS. 10a and 10b shows schematically in side elevation view a multiple function cannula and thermal ablation probe system which also includes provision for other functionality such as a tissue biopsy prior to, during, or after the ablation.
Figure 10B:
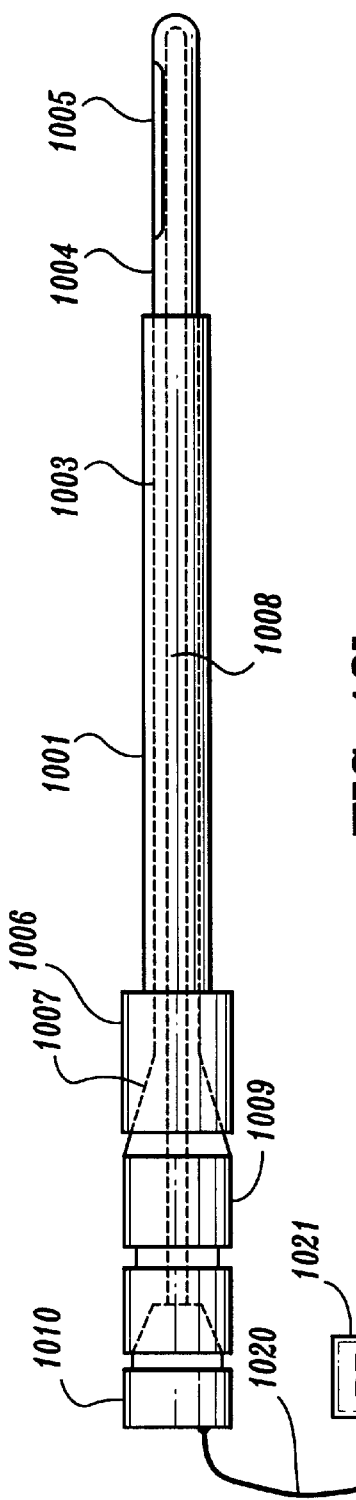

FIG. 10 shows a system of thermosurgery cannulae and electrodes together with other instrumentation which can be used to complement and augment the process. As an illustration, in the upmost illustration in FIG. 10 is shown a cannula 1001 which is insulated over a substantial portion of its length. It has a hub 1006 with a luer taper 1007. This cannula can be inserted into the body, freehand or stereotactically, percutaneously or intraoperatively, with, for example, a sharpened stylet in place as illustrated in connection with FIG. 2. Then, a second cannula 1003 may be inserted into cannula 1001, and the hub 1009 of cannula 1003 can match with the luer 1007 to seal the two cannulae together at their hubs. The tip of cannula 1003 is shown as 1004 and has a side window 1005, as indicated in FIG. 10. This window could actuate as a biopsy needle, or aspirating device, or suction tube device, or side-scanning ultrasonic detector or radar system. Such side-cutting or windowed type biopsy needles are known in the industry and illustrated by the NBN Nashold Biopsy Needle of Radionics, Inc., Burlington, Mass. Inside the cannula 1003, a third cannula 1008 can be introduced which can give a radiofrequency connection via the connection unit 1002 to an external radiofrequency, or high frequency generator, or laser generator 1021. Thus, this combination illustrates an example of a multi-purpose cannula, biopsy needle system, and high frequency lesioning system. Inside cannula 1008 can also be a cooling device which would have connections (not shown) through the hub 1010 to give a cooled-tip type radiofrequency heating electrode. The tip 1004 may be in part uninsulated so that electric current lines emanating from it, once connected to an external high voltage generator, can give rise to ablative heating as described in the parent application and in this continuation-in-part application.

In the lower figure of FIG. 10 is a variation of the apparatus and usage in the upper portion of FIG. 10 wherein the same cannula 1001 is depicted. Inserted as an alternative to the biopsy cannula 1003 of the upper figure, there is inserted another cannula 1030 which may be a pure heating or high frequency cannula with exposed tip 1031 and hub 1033. The hub 1033 matches to the hub 1006 of the insertion cannula 1001 via the luer structure or tapered hub structure 1007. Thus, connection means such as 1035 to a coolant inflow and outflow system with coolant fluid control and supply and reservoir system indicated by structure 1036 may be in place. Also, a connection 1038 made to the hub 1033 of the high frequency cannula 1030 can connect to an external generator 1037 of high frequency power to implement the heating process or the thermosurgical ablation. Thus, FIG. 10 illustrates a multi-modal, or multi-structured, or separable-structured system which includes an insertion cannula, a biopsy or other surgical purpose device, and a high frequency probe, all illustrated in one multiple-purpose system.

It is noted in FIG. 10 that the length L of the high-frequency tip exposed portion 1031 affects the size of the ablation volume. Thus, by choosing the appropriate length of the shaft 1030 in accordance with the shaft length of 1001, the exposed tip length L can be selected or adjusted by the operator, and this is claimed as part of the invention.

Figure 11:
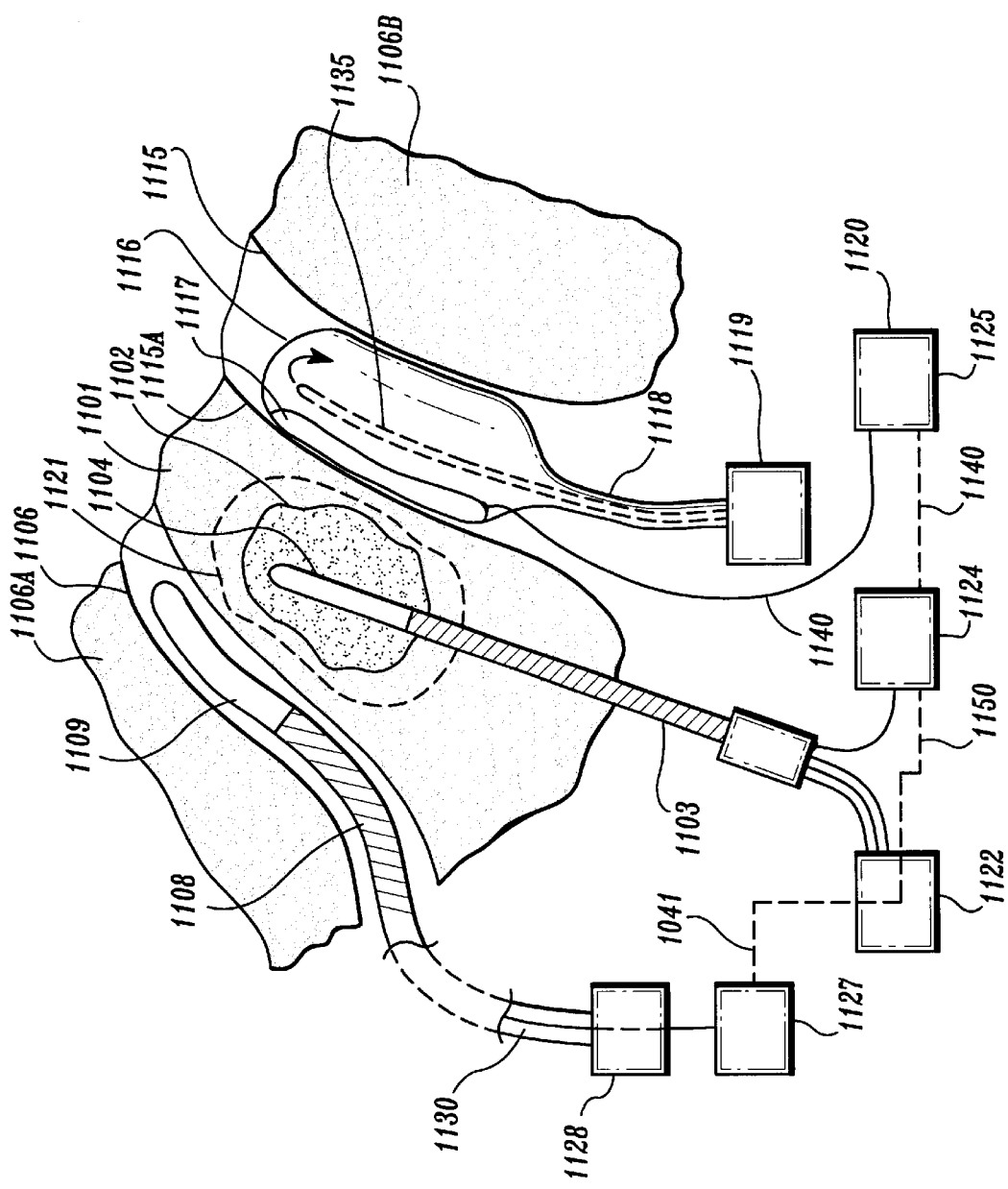
FIG. 11 shows a schematic arrangement of a thermosurgery probe in conjugation with other electrodes or probe, some of which may be cooled, which can be used to modify the thermal ablation volume while protecting delicate structures in the vicinity.

FIG. 11 shows an embodiment of a complex of heating and cooling electrodes which can be used to approach a complex structure within the body and define heat and cooling boundary conditions so as to shape the ablation volume. This example is meant to show the variability of approaches and embodiments possible with the parent application and this continuation-in-part. The bodily tissue might be represented by the masses 1106A, 1101, and 1106B, and there may be orifices or channels such as 1106 and 1115 within or running into or through the tissue. For example, 1106 may be the urethra of the patient, and 1115 may be the rectum. Alternatively, these passages may be large blood vessels or channels such as the aorta or liver, arterial or venous supplies, or the pancreas or liver aqueducts, or the ventricular channels and aqueducts in the brain. Through these openings, whether they be manmade or natural, electrodes can be placed such as the electrode 1109 in channel 1106, or the inflatable, conformal electrode 1117 which has a surface against the wall 1115A where the electrode surface represented by 1117 comes into electrical or thermal contact with the wall of 1115A. The rest of the structure 1116 may, for example, be an inflatable, fluid-filled balloon-like structure or condom-like structure, possibly insulated over much of its surfaces Furthermore, a tissue-penetrating electrode structure such as 1103 with insulative shaft represented by the hatched area may be inserted through the tissue percutaneously or intraoperatively into a target region 1102, with the exposed high frequency electrode being indicated by the tip 1104. Each of these electrodes may be connected to separate or common high frequency, RF, or laser sources or other forms of heat-sending or power-producing devices. For example, electrode 1108 is connected back via the channel 1130, in this case a catheter-like structure to the cooling supply or control unit 1128, which in turn may be connected onto a high frequency source 1127. Similarly, electrode 1103 may be connected back to a cooling supply 1122 and radiofrequency supply 1124. The electrode contact 1117 may be connected via electrical connection 1140 to a high frequency source 1120. The high frequency sources 1127, 1124, and 1120 may all be connected together, as via the dashed lines 1140, 1150, and 1140, or they may be at different poles of bipolar arrangements of the electrodes, or they may be connected in varying alternating phased relationship in time so that one is at high frequency potential at a different time or phase cycle than the others to create various heating effects at different times in different places. Each may or may not have a cooled tip electrode; for example with the structure 1116 with its electrode structure 1117, there is an internal fluid-carrying channel shown by 1135 which may produce circulation, as shown by the arrow, with a return duct so that the entire bag structure 1116 may be cooled. Whereas although the heating power deposition is produced in the tissue of 1101 nearest to or in proximity to 1117 with a cooled boundary condition imposed by the coolant circulation in bag 1116 to essentially keep the wall 1115A cool, the tissue on the wall 1115 is not destroyed during the thermosurgery. A tumor or other anatomical structure, indicated by the solid line 1102, may be the target volume or tissue volume to be destroyed or ablated. By use of proper cooling boundary conditions and electromagnetic boundary conditions between this complex of electrodes shown, it may be that the heat ablation zone, indicated for example by the kill isotherm 1121 as a dashed line, may engulf the target volume 1102, and yet the delicate tissues associated with the channel 1106 and 1115A may not be destroyed because they are kept cool by the cooled tip character of electrode 1109 and 1116, respectively. Also, the electrode tip 1104 may have a cooled tip character so that the thermal distribution is thrown away from it to larger distances. For example, in the prostate, the electrode 1109 may be a cooled tip catheter type electrode in the urethra, and the rectal probe 1116 may also be cooled substantially. The electrode 1104 may be pierced through the rectal wall, into the prostate, to the appropriate region of the prostate where a cancerous tumor has been visualized by imaging. By the appropriate cooling of the respective electrodes, a volume of ablation may be produced such as 1121 which engulfs the cancerous prostate tumor and yet spares the delicate mucous membrane 1115A of the rectum and the delicate urethra 1106 or seminal vesicles near 1106. By appropriate simultaneous or post heating imaging, the extent and volume of the lesion or ablation volume may be visualized directly, and the cancerous tumor can be engulfed and destroyed safely while assuring that the other delicate normal structures around the tumor are not damaged. The electrode 1117 may be the reference or indifferent electrode associated with an RF circuit between the RF generator 1124 and the reference electrode 1117, and the active electrode being 1104. Element or catheter tip 1109 may also be an RF electrode for heat deposition to properly spread out the heat volume. A similar scenario could be devised in the internal organs such as the liver, pancreas, heart, brain, intestines, or other organs. A flexible catheter such as 1109 can be inserted through a vessel, for example in the groin or percutaneously into the hepatic vessels or the duct within the pancreas, and a second electrode 1104 can be pierced into a tumor which lies nearby. By cooling 1009, the delicate aqueduct or channel may be spared from ablation, whereas the tumor 1102 may be totally destroyed under direct visualization and under appropriate preplanning to predict the amount of power and cooling necessary to do the appropriate ablation. Other scenarios such as in the pancreas can be devised by those skilled in the art where the electrode 1116 may be the active electrode and may represent a stint or a balloon or a condom-like structure that can be put into the pancreatic duct, and by appropriate cooling in conjugation with RF heating, it can "throw" the heat into a pancreatic tumor while sparing the structure of the duct to preserve normal processing of biological fluids. Also noteworthy is the use of cooled boundary condition electrodes such as 1109 and 1117 in the presence of a heat-throwing electrode such as 1104 can "repel" the heat from critical structures, and thus one can tailor the shape of the ablation volume as desired.

It is manifest in connection with the discussion of FIG. 11 and the parent application that the use of multiple radiofrequency or high frequency or laser electrodes, some of which have perfusion cooling and others which do not, or perfusion boundary condition electrodes which may or may not have high frequency power associated with them, can be used in conjugation. This methodology of multiple electrodes used in bipolar arrays, sequenced bipolar arrays, monopolar sequenced arrays, phased arrays are all included with the scope of this continuation-in-part application and the parent application.

Also included within the scope of this patent is the use of contrast agents, either for CT or MRI imaging. The time of administration of contrast agents can be varied by those skilled in the art. For example, it can be administered into the patient prior to the imaging and prior to the thermal ablation so as to watch the process thereafter, or it can be administered after thermal ablation to then observe the effect of the ablation seconds, minutes, or contemporaneously with the thermal ablation itself. Those skilled in the art in using contrast agent of various kinds and compositions and mixtures and with given chronological sequencing relative to the thermal ablation and various imaging stages can devise other variations, however, these are all claimed to be within the scope of the present continuation-in-part and parent applications for thermal surgery. Those skilled in the art can devise many variations of the cooled tip thermosurgery invention and other invention concepts which are described in this continuation-in-part and also the parent application by the present authors. For example, a variety of geometries of high frequency, laser, radiofrequency, boundary condition cooling devices, temperature clamped active electrodes, multi-polar and phased electrode arrays, characteristics of high frequency power generators, thermometric readout means, placement of multiple thermometric sensing devices of various kinds, varying geometries of active or inactive high frequency electrodes including off-axis electrodes such as the Zervas Hypophysectomy Kit of Radionics, Inc., Burlington, Mass., or inflatable electrodes or basket-type electrodes or flexible, large-area, tipped electrodes connected to-stiff-shafted or catheter-type electrodes, all of which can be devised by those skilled in the art are claimed within the scope of the present invention. A variety of usages of image scanning means in conjugation with this technology to perform preplanning, contemporaneous monitoring, or post-thermosurgery monitoring and evaluation can be devised by those skilled in the art. The use of CT, angiographic, MRI, PET, SPECT, MEG, ultrasonic, or sonic monitoring and imaging can all be used in conjugation with the present invention, examples of which are described here, and these are claimed as part of the method and apparatus associated with the present invention herein. Graphing of parameters and control parameters and system parameters associated with the thermal ablation process, both in analog, digital, or graphical form are included within the scope of the present invention. A variety of methods of preplanning and displaying or graphically rendering the estimated isotherms in one-, two-, or three-dimensional representations are time-dependent representations are all included within the present invention, including finite element methods, analytic methods, conformal mapping, time-dependent methods, relaxation methods, solutions to Laplace and Poisson's equation, etc., which are familiar to those skilled in mathematical physics and those skilled in the art. Graphic renderings of the control parameters, together or in sequence, are known to those skilled in computer art and are included within the scope of the present invention. Site-specific configurations of electrodes and electrode geometries, for example for the liver, prostate, brain, lung, pancreas, and appropriate geometry of electrodes together with consistent heating and cooling parameters can be devised by those skilled in the clinical or electromechanical art. Many of the system aspects and structures illustrated herein can be applied to cooled-tip RF electrodes or non-cooled-tip RF probes, and these are claimed here for either application or case. As an example, the systems, methods, and apparatus shown in FIGS. 6, 7, 8, 9, and 11 are novel for cooled or non-cooled probes, and both situations are claimed here. It is also true that in all of the examples, the cooling fluid or agent may be turned off and on to suit the situation, and such sequential thermosurgery by, for instance, making a heat ablation without cooling, and then making a heat ablation with cooling may have clinical advantages. For instance, a local or near ablation may be done by the former, followed by a distant or far ablation done by the latter, in combination, to get full ablation coverage. This is also claimed herein. It is noted that although the Figures herein show us most cases, a straight, rigid, tubular shaped electrode, probe, shaft, cannulae, etc., these could be shown as flexible, catheter-like, steerable, contourable, inflatable balloon-like, or other shaped electrodes or probe structures—these other shapes are also claimed herein.

It is claimed in the invention, without limitation, that the cannula, RF probe, cooling element, thermosensing, stylet elements, etc., illustrative examples of which have been described here and in the parent application, may be used in any combination or grouping. For example, we claim the use of a separable cannula, as in FIGS. 1 and 2, with a separable RF probe element to supply connection to the RF generator, but without a cooling element or a thermo-sensing element. In such case, the operator may do an ablation while controlling only RF power and knowing the tip geometry. Another example claimed here is the use of a cannula with a separable cooling element and/or an RF element, or each of a separable RF and separable cooling elements to do an ablation. The operator may use the procedure of just controlling some RF generator parameter, such as power, current, voltage, impedance (or a combination of these), and use simple ice water or room temperature saline injected into the cooling element to cool the tip, but not monitor coolant temperature or tip or tissue temperature. There may or may not be measurement of tip, tissue, or coolant temperature. There may or may not be measurement of tip, tissue, or coolant temperature if the ablation is being done for example in a target area which is not critical or if real-time or post-image monitoring of the ablation volume is being done so as to check, limit, or incrementally increase the ablation volume by some other measurement or method.

We claim here the separability of cannula (or catheter) electrode (or probe), stylet or obdurator, power unit (RF, laser, etc.), cooling element (if used at all), temperature-sensing elements which have the novel advantages of reducing disease transmission (especially since one objective is cancer cell penetration in sick patients (many with AIDS, greater economy, disposability of less expensive elements, great flexibility in inventorying different cannula tip exposures, cleaning, storage, multiple serial or parallel usage in the same patient and for tumor volume, durability, reliability, factory sharpness (of tips for instance), use of stiff stylets during insertion for great accuracy (especially for deep or insertion-resistant targets), and other reasons mentioned herein or which can be elucidated by those skilled in the art.

We also claim the use of a high frequency probe with or without a cooling element in it for application against an organ, bodily opening, passageway, vessel, duct, etc, or against the external skin surface. This could then ablate by heating a tumor or other tissue near the electrode. If cooling were applied, then the tissue immediately near the electrode could be cooled and protected against ablation. For instance, a tumor below the skin or near an internal tissue could be destroyed by heat while the skin or tissue proximal to the electrode could be spared. Colon tumors might be destroyed by an inflatable or surface type electrode pressed or laid against the colon; and by cooling the electrode, the heat could be "thrown" into tumor, which might be in the colon wall, without completely destroying the colon wall itself. Similar arrangements could be devised and planned by those skilled in the art for other organs, and all these are claimed here and in the parent application.

It is also possible to both force fluid into the cooling element under positive pressure, and at the same time to pull the fluid out of the cooling element by a negative pressure. For instance, in FIG. 1 a positive coolant fluid pressure applied on the inlet fluid could force the coolant into inlet port 107, and a negative coolant fluid pressure applied on the outlet fluid could pull the fluid out of port 108. The fluid supply system could thus include a "push" and a "pull" device to do this, all regulated by input and output pressure control. For instance, a peristaltic pump could both push the fluid in and pull the fluid out. Such a distal pressure system could increase the cooling fluid throughput to the electrode, and thus increase cooling efficiency. For small gauge or long length cannulae or catheters, this may be important for adequate cooling.

It is also noted and claimed in this and the parent application the method of making a two-stepped lesion; one which uses the cooled-tip electrode to make a large ablation, and combined with a second ablation step where the cool-tip is turned off, i.e. there is little or no cooling of the tip, in which case a standard lesion or ablation is made. The latter, smaller ablation will "fill-in" the entire ablation volume to include the near region (near the tip) as well as the distant region (farther away from the tip when the perfused or cool tip is on), so that no cancer cells, for instance, will survive anywhere in the volume.

It is also claimed in this and the parent application the use of the cooled-tip electrode in the heating in the spine. This could include heating facet joints, spinal nerves, and/or the intervertebral disc itself. In each case, a larger "lesion" can be made for a given electrode size than without a cooled-tip. In heating the disc, for example, it may be required to heat more extensively the entire disc space, and this can be done effectively with a cool-tip RF electrode. The cool-tip electrode could be inserted permanently into the disc space in the way described by Sluijter and Cosman, U.S. Pat. No. 5,433,739, Jul. 18, 1995, and more extended disc lesion could be made to more fully denervate the disc volume.

We claim also here the use of a closed radiofrequency or high frequency probe, having a closed distal tip that is used to penetrate or press or contact the patient's body, and which has an open proximal end for insertion of other probes or fluids. Referring to FIG. 4 again, there is the cannula 401 which has the closed distal tip 403A and has an opening at its proximal end 421. This kind of radiofrequency (rf) or high frequency (hf) probe has never been seen before in prior art. Typically, previous rf probes either had a cannula with an open distal tip or the entire probe was closed on both of its distal and proximal ends. Thus we wish to claim here the kind of rf or hf cannula shown as one embodiment in FIG. 4. Any of many kinds of secondary elements could be inserted into or coupled to the open proximal cannula end, such as the cooling elements, or rf thermosensing elements as illustrated in FIG. 4, or any other kind of function probe. The closed tip probe could either be rigid, straight, curved, flexible, and so on, as may be devised by those skilled in the art. The closed tip may be sharpened or non-sharp depending on the application—viz., used for tissue self-penetration or used for contact against non-cutting tissue penetration.

Having described the embodiments above of the present invention and that of the parent invention, what we claim by U.S. Letters Patent are the following:

1. A process for the controlled ablation of tissue in the body of a subject, comprising the steps of:
   providing a housing having a portion of its surface forming a high frequency electrode and defining an inner space;
   inserting an inner probe into the inner space to define a channel within the inner space;
   supplying high frequency electrical energy to the outer housing for the ablation of tissue in the body of the subject;
   providing circulating coolant through the channel;
   monitoring audio signals, positioning a microphone adjacent the tissue and detecting the audio signals emitted by the tissue using the microphone during an ablation procedure, emanating from the tissue in the body of the subject representative of physiological changes caused by the ablation; and
   dynamically controlling and maintaining a degree of high frequency electrical energy supplied to the outer housing, the degree being responsive to indications of the audio signals emanating from the body of the subject.

2. The process in accordance with claim 1 further including the step of providing an insulation material over a substantial portion of the housing to prevent ablation of tissue in the body of a subject contiguous to the insulation material.

3. The process in accordance with claim 1 wherein the step of providing includes incorporating the microphone in the housing.

4. The process in accordance with claim 1 further including the step of displaying a graphic image of the audio signals.

5. The process in accordance with claim 1 further including the step of imaging the tissue during the ablation procedure with imaging means selected from the group consisting of ultrasound, CT, MRI, and PET imaging modalities.

6. The process in accordance with claim 5 further including the step of displaying a graphic image of the tissue produced by the imaging devices.

7. The process in accordance with claim 6 further including the step of displaying a previously scanned image of a tumor's volume superimposed on the graphic image of the tissue.

8. A process for the controlled ablation of tissue in the body of a subject, comprising the steps of:
   providing a housing having a portion of its surface forming a high frequency electrode and defining an inner space;
   inserting an inner probe into the inner space to define a channel within the inner space;
   supplying high frequency electrical energy to the outer housing for the ablation of tissue in the body of the subject; wherein the high frequency electrode further comprises a first hemispherical portion and a second opposed hemispherical portion wherein the first hemispherical portion is electrically conductive and the second hemispherical portion is electrically insulated and wherein, during the step of supplying, the first hemispherical portion causes ablation of tissue adjacent thereto that extends in a direction opposite the second hemispherical portion;
   providing circulating coolant through the channel; monitoring audio signals, during an ablation procedure, emanating from the tissue in the body of the subject representative of physiological changes caused by the ablation; and
   dynamically controlling and maintaining a degree of high frequency electrical energy supplied to the outer housing, the degree being responsive to indications of the audio signals emanating from the body of the subject.

9. A process for the controlled ablation of tissue in the body of a subject, comprising the steps of:
   providing a housing having a portion of its surface forming a high frequency electrode and defining an inner space;
   inserting an inner probe into the inner space to define a channel within the innerspace;
   supplying high frequency electrical energy to the outer housing for the ablation of tissue in the body of the subject; wherein the housing comprises an outer cannula having a closed tip portion disposed at its distal end, the tip portion further comprising a first hemispherical portion and a second opposed hemispherical portion, the first hemispherical portion forming the high frequency electrode and the second hemispherical portion being insulated and wherein, during the step of supplying, the first hemispherical portion causes ablation of tissue adjacent thereto that extends in a direction opposite the second hemispherical portion;
   providing circulating coolant through the channel;
   monitoring audio signals, during an ablation procedure, emanating from the tissue in the body of the subject representative of physiological changes caused by the ablation; and
   dynamically controlling,.and maintaining a degree of high frequency electrical energy supplied to the outer housing, the degree being responsive to indications of the audio signals emanating from the body of the subject.

10. The process in accordance with claim 9 wherein the insulated tip portion and the electrically conductive tip portion each comprise approximately one half the periphery of the tip portion.

11. The process in accordance with claim 9, further including the step of displaying a graphic image of the audio signals.

12. The process in accordance with claim 9, further including the step of imaging the tissue during the ablation procedure with imaging means selected from the group consisting of ultrasound, CT, MRI, and PET imaging modalities.

13. The process in accordance with claim 12 further including the step of displaying a graphic image of the tissue produced by the imaging devices.

14. The process in accordance with claim 13 further including the step of displaying a previously scanned image of a tumor's volume superimposed on the graphic image of the tissue.

* * * * *